United States Patent
Diolaiti

(10) Patent No.: US 11,969,147 B2
(45) Date of Patent: Apr. 30, 2024

(54) SYSTEM AND METHOD FOR MULTI-MODE IMAGING DEVICE CONTROL

(71) Applicant: INTUITIVE SURGICAL OPERATIONS, INC., Sunnyvale, CA (US)

(72) Inventor: Nicola Diolaiti, Menlo Park, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 59 days.

(21) Appl. No.: 17/678,843

(22) Filed: Feb. 23, 2022

(65) Prior Publication Data

US 2022/0175230 A1 Jun. 9, 2022

Related U.S. Application Data

(62) Division of application No. 16/775,259, filed on Jan. 28, 2020, now Pat. No. 11,284,782, which is a (Continued)

(51) Int. Cl.
*A61B 1/00* (2006.01)
*A61B 1/008* (2006.01)
(Continued)

(52) U.S. Cl.
CPC ...... *A61B 1/00042* (2022.02); *A61B 1/00149* (2013.01); *A61B 1/008* (2013.01);
(Continued)

(58) Field of Classification Search
CPC ......... A61B 34/30; A61B 34/35; A61B 34/37; A61B 34/74; A61B 34/76; A61B 34/77;
(Continued)

(56) References Cited

U.S. PATENT DOCUMENTS

| 4,655,567 A | 4/1987 | Morley |
| 4,832,473 A | 5/1989 | Ueda |

(Continued)

FOREIGN PATENT DOCUMENTS

| JP | S57190549 A | 11/1982 |
| JP | 2000166936 A | 6/2000 |

OTHER PUBLICATIONS

Ikuta, Koji et al., "Development of remote microsurgery robot and new surgical procedure for deep and narrow space," Proc. IEEE International Conference on Robotics & Automation, 2003, pp. 1103-1108, vol. 1, IEEE.

(Continued)

*Primary Examiner* — Timothy J Neal
(74) *Attorney, Agent, or Firm* — Artegis Law Group, LLP

(57) ABSTRACT

Techniques for multi-mode imaging device control include determining, by a controller, if an orientational mode command or a translational mode command is entered; in response to determining that the orientational mode command is entered, constraining, by the controller, movement of an imaging device so that a focal point of the imaging device moves along a concave virtual surface in response to translational movement of one or more input devices; and in response to determining that the translational mode command is entered, causing, by the controller, translational movement of the imaging device in a three-dimensional space in response to the translational movement of the one or more input devices.

20 Claims, 15 Drawing Sheets

Related U.S. Application Data division of application No. 15/935,936, filed on Mar. 26, 2018, now Pat. No. 10,582,838, which is a division of application No. 14/918,695, filed on Oct. 21, 2015, now Pat. No. 9,955,859, which is a division of application No. 12/163,051, filed on Jun. 27, 2008, now Pat. No. 9,179,832.

(51) Int. Cl.
| | |
|---|---|
| A61B 1/045 | (2006.01) |
| A61B 1/05 | (2006.01) |
| A61B 1/313 | (2006.01) |
| A61B 34/00 | (2016.01) |
| A61B 34/30 | (2016.01) |
| A61B 34/35 | (2016.01) |
| A61B 34/37 | (2016.01) |
| A61B 17/00 | (2006.01) |
| A61B 34/20 | (2016.01) |
| A61B 90/00 | (2016.01) |
| A61B 90/30 | (2016.01) |

(52) U.S. Cl.
CPC .............. *A61B 1/045* (2013.01); *A61B 1/05* (2013.01); *A61B 1/313* (2013.01); *A61B 1/3132* (2013.01); *A61B 34/30* (2016.02); *A61B 34/35* (2016.02); *A61B 34/37* (2016.02); *A61B 34/74* (2016.02); *A61B 34/76* (2016.02); *A61B 34/77* (2016.02); *A61B 2017/00296* (2013.01); *A61B 2034/2057* (2016.02); *A61B 2034/301* (2016.02); *A61B 2034/305* (2016.02); *A61B 2090/306* (2016.02); *A61B 90/361* (2016.02)

(58) Field of Classification Search
CPC ..... A61B 1/00149; A61B 1/008; A61B 1/045; A61B 1/05; A61B 1/313; A61B 1/3132
See application file for complete search history.

(56) References Cited

U.S. PATENT DOCUMENTS

| | | | |
|---|---|---|---|
| 4,994,079 A | | 2/1991 | Genese et al. |
| 5,116,180 A | | 5/1992 | Fung et al. |
| 5,159,446 A | * | 10/1992 | Hibino ............... A61B 1/00042 600/152 |
| 5,285,525 A | | 2/1994 | Nagao et al. |
| 5,417,210 A | * | 5/1995 | Funda ................... A61B 90/10 600/109 |
| 5,439,005 A | | 8/1995 | Vaughn |
| 5,582,617 A | | 12/1996 | Klieman et al. |
| 5,609,565 A | | 3/1997 | Nakamura |
| 5,792,164 A | | 8/1998 | Lakatos et al. |
| 5,825,432 A | | 10/1998 | Yonezawa |
| 5,876,325 A | | 3/1999 | Mizuno et al. |
| 5,894,322 A | | 4/1999 | Hamano et al. |
| 6,013,024 A | | 1/2000 | Mitsuda et al. |
| 6,066,090 A | | 5/2000 | Yoon |
| 6,352,503 B1 | | 3/2002 | Matsui et al. |
| 6,428,487 B1 | | 8/2002 | Burdorff et al. |
| 6,572,629 B2 | | 6/2003 | Kalloo et al. |
| 6,627,673 B2 | | 9/2003 | Topolkaraev et al. |
| 6,761,685 B2 | | 7/2004 | Adams et al. |
| 6,799,065 B1 | | 9/2004 | Niemeyer |
| 6,988,985 B2 | | 1/2006 | Suzuki et al. |
| 6,988,987 B2 | | 1/2006 | Ishikawa et al. |
| 6,991,602 B2 | | 1/2006 | Nakazawa et al. |
| 7,029,435 B2 | | 4/2006 | Nakao |
| 7,060,024 B2 | | 6/2006 | Long et al. |
| 7,070,559 B2 | | 7/2006 | Adams et al. |
| 7,155,315 B2 | | 12/2006 | Niemeyer et al. |
| 7,371,210 B2 | | 5/2008 | Brock et al. |
| 7,537,561 B2 | | 5/2009 | Yamaya et al. |
| 7,549,984 B2 | | 6/2009 | Mathis |
| 7,608,083 B2 | | 10/2009 | Lee et al. |
| 7,670,282 B2 | | 3/2010 | Mathis |
| 7,918,845 B2 | | 4/2011 | Saadat et al. |
| 7,942,868 B2 | | 5/2011 | Cooper et al. |
| 7,955,340 B2 | | 6/2011 | Michlitsch et al. |
| 8,216,252 B2 | | 7/2012 | Vaughan et al. |
| 8,236,010 B2 | | 8/2012 | Ortiz et al. |
| 8,277,373 B2 | | 10/2012 | Maahs et al. |
| 8,587,517 B2 | | 11/2013 | Perkunder |
| 8,740,885 B2 | | 6/2014 | Larkin et al. |
| 9,179,832 B2 | | 11/2015 | Diolaiti |
| 9,955,859 B2 | | 5/2018 | Diolaiti |
| 10,582,838 B2 | | 3/2020 | Diolaiti |
| 2002/0133173 A1 | | 9/2002 | Brock et al. |
| 2002/0140814 A1 | | 10/2002 | Cohen-Solal et al. |
| 2003/0055410 A1 | | 3/2003 | Evans et al. |
| 2004/0249367 A1 | | 12/2004 | Saadat et al. |
| 2005/0065401 A1 | | 3/2005 | Saadat et al. |
| 2005/0107663 A1 | | 5/2005 | Saadat et al. |
| 2005/0203382 A1 | | 9/2005 | Govari et al. |
| 2006/0178556 A1 | | 8/2006 | Hasser et al. |
| 2006/0178560 A1 | | 8/2006 | Saadat et al. |
| 2007/0198008 A1 | | 8/2007 | Hauck et al. |
| 2008/0064921 A1 | | 3/2008 | Larkin et al. |
| 2008/0065105 A1 | | 3/2008 | Larkin et al. |
| 2008/0065108 A1 | | 3/2008 | Diolaiti |
| 2008/0106523 A1 | | 5/2008 | Conrad |
| 2009/0079939 A1 | | 3/2009 | Mimura |
| 2010/0198134 A1 | | 8/2010 | Eckhouse et al. |
| 2020/0163539 A1 | | 5/2020 | Diolaiti |

OTHER PUBLICATIONS

U.S. Appl. No. 13/446,417, "Guide Tube Control of Minimally Invasive Surgical Instruments," Clean Version of Pending Claims, 6 pages.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

\* cited by examiner

SYSTEM AND METHOD FOR MULTI-MODE IMAGING DEVICE CONTROL

RELATED APPLICATIONS

This application is a divisional of U.S. patent application Ser. No. 16/775,259 filed Jan. 28, 2020, which is a divisional of U.S. patent application Ser. No. 15/935,936 filed Mar. 26, 2018 and now U.S. Pat. No. 10,582,838, which is a divisional of U.S. patent application Ser. No. 14/918,695 filed Oct. 21, 2015 and now U.S. Pat. No. 9,955,859, which is a divisional of U.S. patent application Ser. No. 12/163,051 filed Jun. 27, 2008 and now U.S. Pat. No. 9,179,832, each of which is incorporated by reference herein in its entirety for all purposes.

FIELD OF THE INVENTION

The present invention generally relates to medical robotic systems and in particular, to a medical robotic system with image referenced camera control using partitionable orientational and translational modes.

BACKGROUND OF THE INVENTION

Medical robotic systems such as teleoperative systems used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for such medical robotic systems is strong and growing.

One example of such a medical robotic system is the da Vinci Surgical System from Intuitive Surgical, Inc., of Sunnyvale, California, which is a minimally invasive robotic surgical system. The da Vinci® Surgical System has a number of robotic arms that move attached medical devices, such as an image capturing device and Intuitive Surgical's proprietary EndoWrist® articulating surgical instruments, in response to movement of input devices by a surgeon viewing images captured by the image capturing device of a surgical site. Each of the medical devices is inserted through its own minimally invasive incision into the patient and positioned to perform a medical procedure at the surgical site. The incisions are placed about the patient's body so that the surgical instruments may be used to cooperatively perform the medical procedure and the image capturing device may view it without their robotic arms colliding during the procedure.

To perform certain medical procedures, it may be advantageous to use a single entry aperture, such as a minimally invasive incision or a natural body orifice, to enter a patient to perform a medical procedure. For example, an entry guide may first be inserted, positioned, and held in place in the entry aperture. Instruments such as an articulatable camera and a plurality of articulatable surgical tools, which are used to perform the medical procedure, may then be inserted into a proximal end of the entry guide so as to extend out of its distal end. Thus, the entry guide provides a single entry aperture for multiple instruments while keeping the instruments bundled together as it guides them toward the work site.

A number of challenges arise in medical robotic systems using such a bundled unit, however, because of the close proximity of the camera and tool instruments. For example, because the camera instrument has proximal articulations (e.g., joints) that are not visible from the endoscopic camera view, the surgeon can inadvertently drive them to crash into one of the surgical tools while telerobotically moving the camera tip to a different viewing position or orientation. If such a collision occurs, it may cause unwanted motion of the surgical tool(s) that the camera is colliding with and thus potentially harm the patient or otherwise adversely impact the performance of the medical procedure.

Also, since only a limited number of hand-manipulatable input devices are generally available in a medical robotic system, it may be necessary for the operator to temporarily switch association of one of the input devices from its currently associated surgical tool to the camera in order for the operator to telerobotically control positioning of the camera using the input device. Such temporary switching of associations, however, may disrupt the intuitive mapping between the motions of the input device and its associated surgical tool. In particular, it may be necessary to realign the orientation of the input device with that of its associated surgical tool before resuming operation after such temporary switching in order to maintain a sense of telepresence for the surgeon.

OBJECTS AND SUMMARY OF THE INVENTION

Accordingly, one object of one or more aspects of the present invention is a medical robotic system, and method implemented therein, for telerobotically moving an articulatable camera instrument that provides an operator of the system with an awareness of the configuration of the camera instrument's proximal joints.

Another object of one or more aspects of the present invention is a medical robotic system, and method implemented therein, that reduces the risk of a collision between an articulatable camera and other articulatable instruments in close proximity to the camera.

Another object of one or more aspects of the present invention is a medical robotic system, and method implemented therein, that facilitates smooth transitions between switched associations of an input device.

These and additional objects are accomplished by the various aspects of the present invention, wherein briefly stated, one aspect is a medical robotic system comprising: a camera instrument having a viewing tip, a first plurality of joints for moving the viewing tip translationally, and a second plurality of joints for moving the viewing tip orientationally; an input device manually positionable translationally and orientationally; and a controller programmed to actuate the first plurality of joints in response to translational movement of the input device and actuate the second plurality of joints in response to orientational movement of the input device.

Another aspect is a method for controllably moving a tip of an instrument in a direction along a line in three-dimensional space, wherein the tip is movable by a joggle joint assembly having first, second, and third links, a first joint coupling the first and second links, a second joint coupling the second and third links, and a wrist assembly coupling the tip and the third link, wherein the first and third links are constrained to maintain a parallel relationship to each other as the second link rotates about the first joint, and wherein the tip is further movable by an in/out assembly coupled to the first link to move the first link along a longitudinal axis of the first link, the method comprising: actuating the joggle joint assembly to rotate the second link about the first joint so that a tangential component of the rotation is in the direction that the tip is to be moved; and actuating the in/out assembly in coordination with the actuation of the joggle joint assembly in order to move the first link to compensate for a distance of the tip from the line.

Another aspect is a medical robotic system comprising: a camera instrument having a viewing tip, a first plurality of joints for moving the viewing tip translationally, and a second plurality of joints for moving the viewing tip orientationally; an input device manually positionable translationally and orientationally; and a controller programmed to have first and second modes of operation and actuate the first plurality of joints in response to translational movement of the input device when the controller is in the first mode and actuate the second plurality of joints in response to translational movement of the input device when the controller is in the second mode.

Another aspect is a method for moving a camera in response to movement of an input device of a medical robotic system, comprising: constraining the movement of the camera so that its focal point moves along a concave virtual surface until a release is detected.

Another aspect is a medical robotic system comprising: a camera, camera manipulator, input device, and controller. The camera manipulator has a first mechanism for pivoting a line of sight of the camera about a pivot and a second mechanism for positioning the pivot within a three-dimensional space. The controller is configured to receive sensed movement of the input device, cause actuation of the first mechanism in response to the sensed movement until a release is detected, and cause actuation of the second mechanism in response to the sensed movement only after the release is detected.

Another aspect is a method for moving a camera in response to movement of an input device of a medical robotic system, comprising: determining whether either an orientational mode or a translational mode command has been entered by an operator of the medical robotic system; constraining the movement of the camera so that its focal point moves along a concave virtual surface while allowing pivoting of the camera about a pivot if the orientational mode is determined to have been entered; and allowing translational movement of the camera in a three-dimensional space while holding the pivot fixed in the three-dimensional space if the translational mode is determined to have been entered.

Still another aspect is a method for positioning and orienting an articulatable camera instrument extending out of a distal end of an entry guide, comprising: processing and displaying images periodically captured by the articulatable camera instrument on a display screen; disassociating a first input device from a first articulatable tool, and disassociating a second input device from a second articulatable tool; associating the first and second input devices with the articulatable camera instrument; generating an image referenced control from translational movement of the first and second input devices; positioning and orienting the articulatable camera instrument in response to the image referenced command; maintaining orientational alignment between the first input device and the first articulatable tool by feeding back information of an orientation of the first articulatable tool back to the first input device so as to cause orientational movement of the first input device when the first input device and the first articulatable tool are orientationally out of alignment, and maintaining orientational alignment between the second input device and the second articulatable tool by feeding back information of an orientation of the second articulatable tool back to the second input device so as to cause orientational movement of the second input device when the second input device and the second articulatable tool are orientationally out of alignment; disassociating the first and second input devices from the articulatable camera instrument; and re-associating the first input device with the first articulatable tool, and re-associating the second input device with the second articulatable tool.

Additional objects, features and advantages of the various aspects of the present invention will become apparent from the following description of its preferred embodiment, which description should be taken in conjunction with the accompanying drawings.

DETAILED DESCRIPTION OF THE PREFERRED EMBODIMENT

Figure 1:
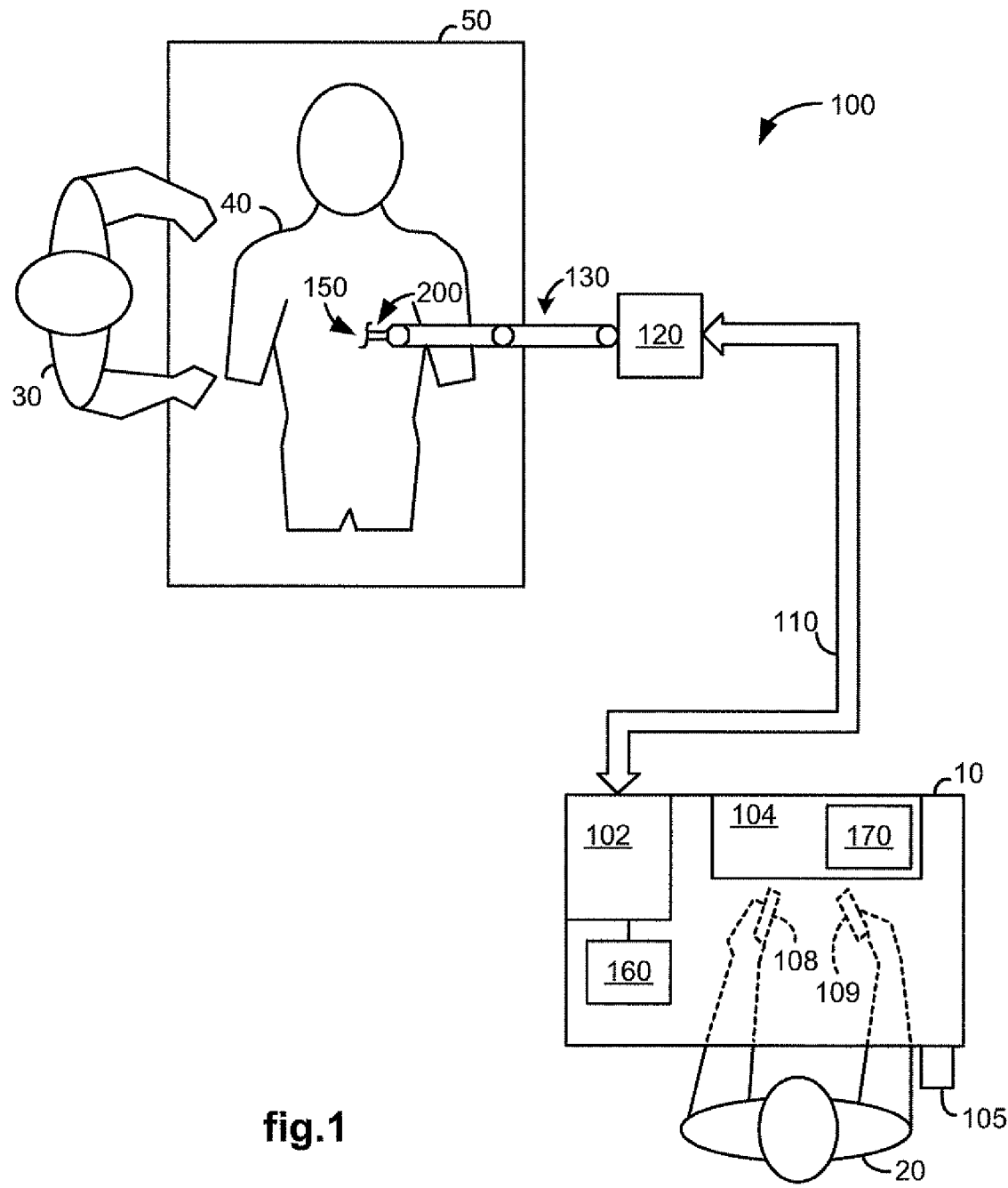
FIG. 1 illustrates a top view of an operating room employing a medical robotic system utilizing aspects of the present invention.

FIG. 1 illustrates, as an example, a top view of an operating room in which a medical robotic system 100 is being utilized by a Surgeon 20 for performing a medical procedure on a Patient 40 who is lying face up on an operating table 50. One or more Assistants 30 may be positioned near the Patient 40 to assist in the procedure while the Surgeon 20 performs the procedure teleoperatively by manipulating input devices 108, 109 on a surgeon console 10.

In the present example, an entry guide (EG) 200 is inserted through a single entry port 150 into the Patient 40. Although the entry port 150 is a minimally invasive incision in the present example, in the performance of other medical procedures, it may instead be a natural body orifice. The entry guide 200 is held and manipulated by a robotic arm assembly 130.

As with other parts of the medical robotic system 100, the illustration of the robotic arm assembly 130 is simplified in FIG. 1. In one example of the medical robotic system 100, the robotic arm assembly 130 includes a setup arm and an entry guide manipulator. The setup arm is used to position the entry guide 200 at the entry port 150 so that it properly enters the entry port 150. The entry guide manipulator is then used to robotically insert and retract the entry guide 200 into and out of the entry port 150. It may also be used to robotically pivot the entry guide 200 in pitch, roll and yaw relative to a longitudinal axis of the entry guide 200 about a pivot point located at the entry port 150. An example of such an entry guide manipulator is the entry guide manipulator 202 of FIG. 2.

The console 10 includes a 3-D monitor 104 for displaying a 3-D image of a surgical site to the Surgeon, left and right hand-manipulatable input devices 108, 109, a foot pedal 105, and a processor (also referred to herein as a "controller") 102. The input devices 108, 109 may include any one or more of a variety of input devices such as joysticks, gloves, trigger-guns, hand-operated controllers, or the like. Other input devices that are provided to allow the Surgeon to interact with the medical robotic system 100 include a foot pedal 105, a conventional voice recognition system 160 and a Graphical User Interface (GUI) 170.

The console 10 is usually located in the same room as the Patient so that the Surgeon may directly monitor the procedure, is physically available if necessary, and is able to speak to the Assistant(s) directly rather than over the telephone or other communication medium. However, it will be understood that the Surgeon can also be located in a different room, a completely different building, or other remote location from the Patient allowing for remote surgical procedures.

Figure 3:
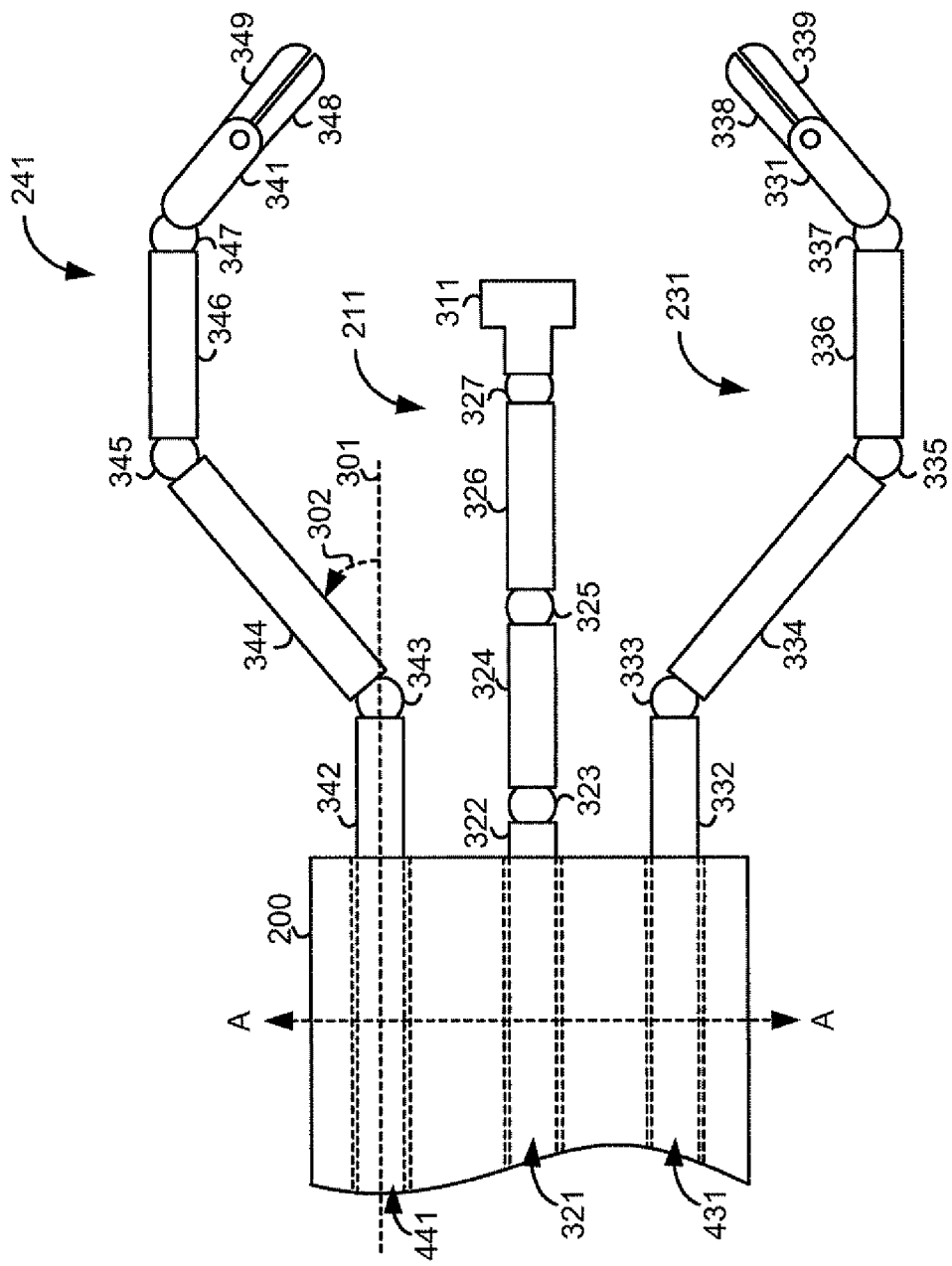
FIGS. 3-4 respectively illustrate top and side views of a distal end of an entry guide with a camera telerobotically controlled by a method utilizing aspects of the present invention.
Figure 4:
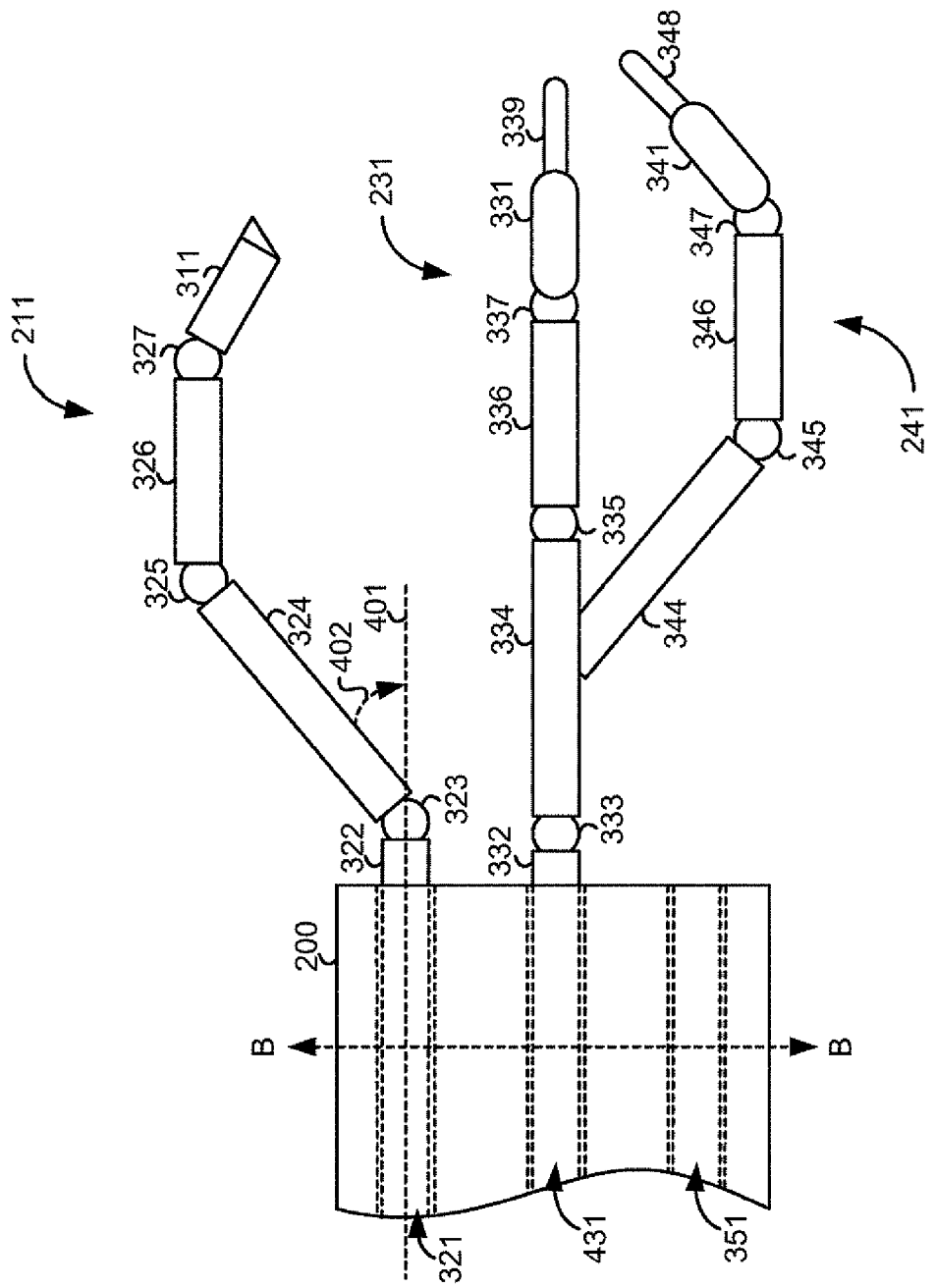
Figure 5:
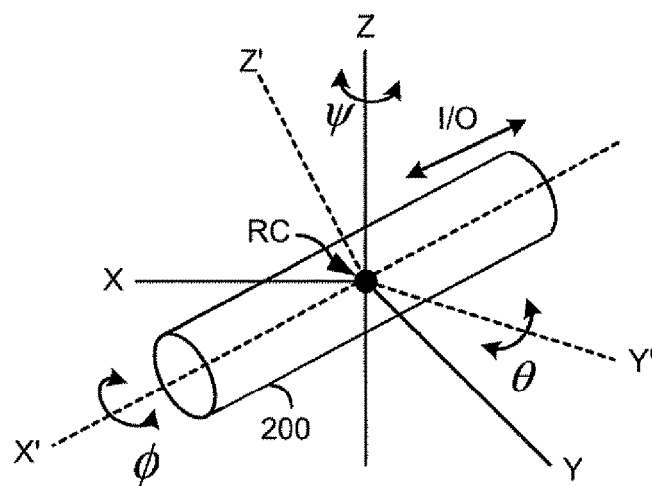
FIG. 5 illustrates a perspective view of an entry guide along with a remote center reference frame and four degrees-of-freedom movement as used in a medical robotic system utilizing aspects of the present invention.
Figure 6:
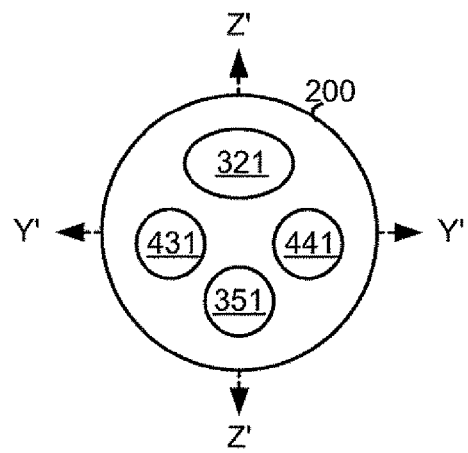
FIG. 6 illustrates a cross-sectional view of an entry guide with passages defined therein that extend between its proximal and distal ends as used in a medical robotic system utilizing aspects of the present invention.

As shown in FIGS. 3-4, the entry guide 200 has articulatable instruments such as surgical tools 231, 241 and a stereo camera 211 extending out of its distal end. Although only two tools 231, 241 are shown, the entry guide 200 may guide additional instruments as required for performing a medical procedure at a work site in the Patient. For example, as shown in FIGS. 4 and 5, passage 351 is available for extending another articulatable instrument through the entry guide 200 and out through its distal end. Each of the surgical tools 231, 241 is associated with one of the input devices 108, 109 in a tool following mode. The Surgeon performs a medical procedure by manipulating the input devices 108, 109 so that the controller 102 causes corresponding movement of their respectively associated surgical tools 231, 241 while the Surgeon views the work site in 3-D on the console monitor 104 as images of the work site are being captured by the camera 211.

Preferably, input devices 108, 109 will be provided with at least the same degrees of freedom as their associated tools 231, 241 to provide the Surgeon with telepresence, or the perception that the input devices 108, 109 are integral with the tools 231, 241 so that the Surgeon has a strong sense of directly controlling the tools 231, 241. To this end, the monitor 104 is also positioned near the Surgeon's hands so that it will display a projected image that is oriented so that the Surgeon feels that he or she is actually looking directly down onto the work site and images of the tools 231, 241 appear to be located substantially where the Surgeon's hands are located.

In addition, the real-time image on the monitor 104 is preferably projected into a perspective image such that the Surgeon can manipulate the end effectors 331, 341 of the tools 231, 241 through their corresponding input devices 108, 109 as if viewing the work site in substantially true presence. By true presence, it is meant that the presentation of an image is a true perspective image simulating the viewpoint of an operator that is physically manipulating the end effectors 331, 341. Thus, the processor 102 may transform the coordinates of the end effectors 331, 341 to a perceived position so that the perspective image being shown on the monitor 104 is the image that the Surgeon would see if the Surgeon was located directly behind the end effectors 331, 341.

The processor 102 performs various functions in the system 100. One important function that it performs is to translate and transfer the mechanical motion of input devices 108, 109 through control signals over bus 110 so that the Surgeon can effectively manipulate and otherwise move devices, such as the tools 231, 241, camera 211, and entry guide 200, that are selectively associated with the input devices 108, 109 at the time.

Although described as a processor, it is to be appreciated that the processor 102 may be implemented in practice by any combination of hardware, software and firmware. Also, its functions as described herein may be performed by one unit or divided up among different components, each of which may be implemented in turn by any combination of hardware, software and firmware. Further, although being shown as part of or being physically adjacent to the console 10, the processor 102 may also comprise a number of subunits distributed throughout the system.

For additional details on the construction and operation of general aspects of a medical robotic system such as described herein, see, e.g., U.S. Pat. No. 6,493,608 "Aspects of a Control System of a Minimally Invasive Surgical Apparatus," and U.S. Pat. No. 6,671,581 "Camera Referenced Control in a Minimally Invasive Surgical Apparatus," which are incorporated herein by reference.

Figure 2:
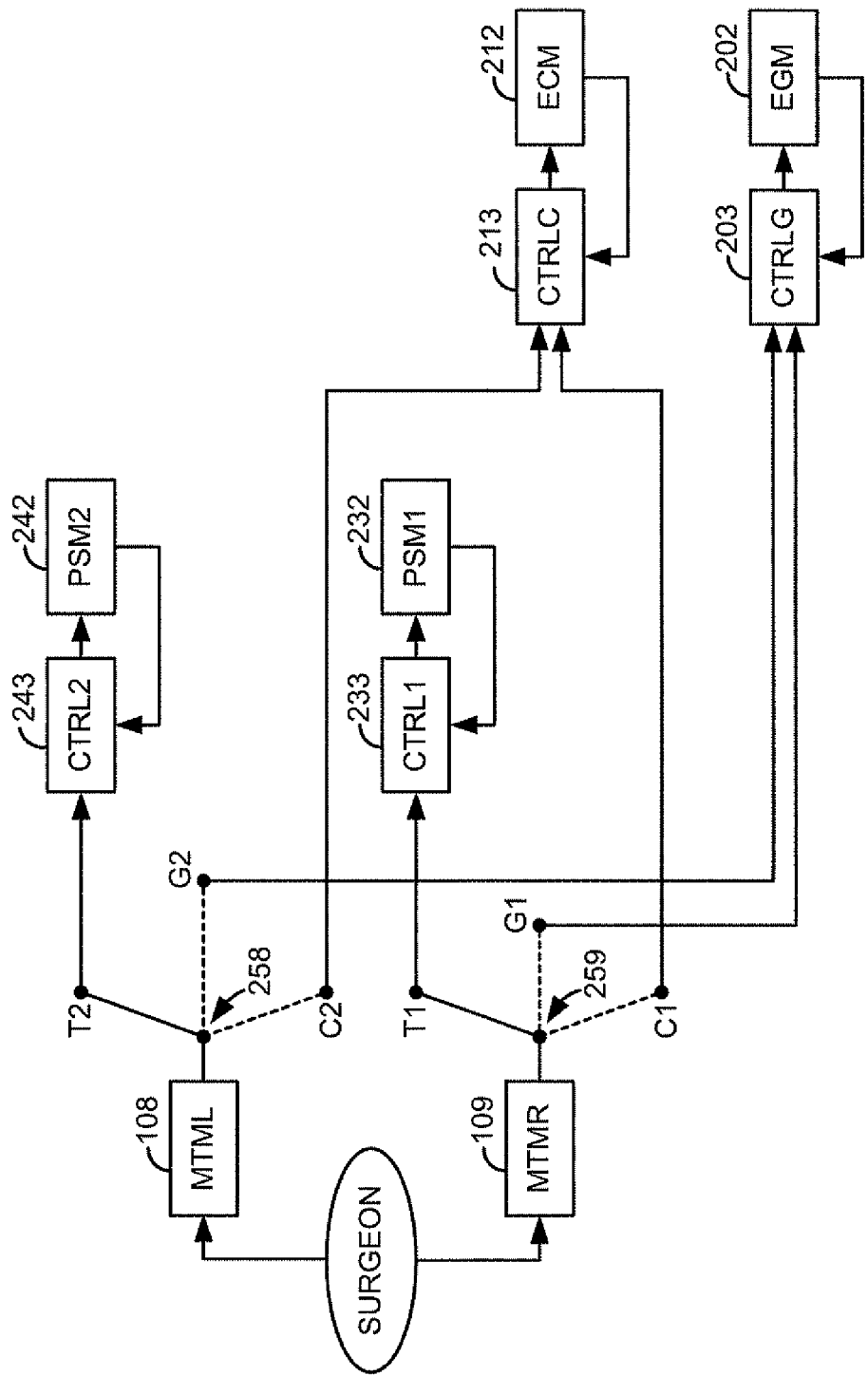
FIG. 2 illustrates a block diagram of components for controlling and selectively associating device manipulators to left and right hand-manipulatable input devices in a medical robotic system utilizing aspects of the present invention.

FIG. 2 illustrates, as an example, a block diagram of components for controlling and selectively associating device manipulators to the input devices 108, 109. Various surgical tools such as graspers, cutters, and needles may be used to perform a medical procedure at a work site within the Patient. In this example, two surgical tools 231, 241 are used to robotically perform the procedure and the camera 211 is used to view the procedure. The tools 231, 241 and camera 211 are inserted through passages in the entry guide 200. As described in reference to FIG. 1, the entry guide 200 is inserted into the Patient through entry port 150 using the setup portion of the robotic arm assembly 130 and maneuvered by the entry guide manipulator (EGM) 202 of the robotic arm assembly 130 towards the work site where the medical procedure is to be performed.

Each of the devices 231, 241, 211, 200 is manipulated by its own manipulator. In particular, the camera 211 is manipulated by a camera manipulator (ECM) 212, the first surgical tool 231 is manipulated by a first tool manipulator (PSM1) 232, the second surgical tool 241 is manipulated by a second tool manipulator (PSM2) 242, and the entry guide 200 is manipulated by an entry guide manipulator (EGM) 202. So as to not overly encumber the figure, the devices 231, 241, 211, 200 are not shown, only their respective manipulators 232, 242, 212, 202 are shown in the figure.

Each of the instrument manipulators 232, 242, 212 is a mechanical assembly that carries actuators and provides a mechanical, sterile interface to transmit motion to its respective articulatable instrument. Each instrument 231, 241, 211 is a mechanical assembly that receives the motion from its manipulator and, by means of a cable transmission, propagates it to the distal articulations (e.g., joints). Such joints may be prismatic (e.g., linear motion) or rotational (e.g., they pivot about a mechanical axis). Furthermore, the instrument may have internal mechanical constraints (e.g., cables, gearing, cams and belts, etc.) that force multiple joints to move together in a pre-determined fashion. Each set of mechanically constrained joints implements a specific axis of motion, and constraints may be devised to pair rotational joints (e.g., joggle joints). Note also that in this way the instrument may have more joints than the available actuators.

In contrast, the entry guide manipulator 202 has a different construction and operation. A description of the parts and operation of the entry guide manipulator 202 is described below in reference to FIG. 7.

In this example, each of the input devices 108, 109 may be selectively associated with one of the devices 211, 231, 241, 200 so that the associated device may be controlled by the input device through its controller and manipulator. For example, by placing switches 258, 259 respectively in tool following modes "T2" and "T1", the left and right input devices 108, 109 may be respectively associated with the first and second surgical tools 231, 241, which are telerobotically controlled through their respective controllers 233, 243 (preferably implemented in the processor 102) and manipulators 232, 242 so that the Surgeon may perform a medical procedure on the Patient while the entry guide 200 is locked in place.

When the camera 211 or the entry guide 200 is to be repositioned by the Surgeon, either one or both of the left and right input devices 108, 109 may be associated with the camera 211 or entry guide 200 so that the Surgeon may move the camera 211 or entry guide 200 through its respective controller (213 or 203) and manipulator (212 or 202). In this case, the disassociated one(s) of the surgical tools 231, 241 is locked in place relative to the entry guide 200 by its controller. For example, by placing switches 258, 259 respectively in camera positioning modes "C2" and "C1", the left and right input devices 108, 109 may be associated with the camera 211, which is telerobotically controlled through its controller 213 (preferably implemented in the processor 102) and manipulator 212 so that the Surgeon may position the camera 211 while the surgical tools 231, 241 and entry guide 200 are locked in place by their respective controllers 233, 243, 203. If only one input device is to be used for positioning the camera, then only one of the switches 258, 259 is placed in its camera positioning mode while the other one of the switches 258, 259 remains in its tool following mode so that its respective input device may continue to control its associated surgical tool.

On the other hand, by placing switches 258, 259 respectively in entry guide positioning modes "G2" and "G1", the left and right input devices 108, 109 may be associated with the entry guide 200, which is telerobotically controlled through its controller 203 (preferably implemented in the processor 102) and manipulator 202 so that the Surgeon may position the entry guide 200 while the surgical tools 231, 241 and camera 211 are locked in place relative to the entry guide 200 by their respective controllers 233, 243, 213. As with the camera positioning mode, if only one input device is to be used for positioning the entry guide, then only one of the switches 258, 259 is placed in its entry guide positioning mode while the other one of the switches 258, 259 remains in its current mode.

The selective association of the input devices 108, 109 to other devices in this example may be performed by the Surgeon using the GUI 170 or the voice recognition system 160 in a conventional manner. Alternatively, the association of the input devices 108, 109 may be changed by the Surgeon depressing a button on one of the input devices 108, 109 or depressing the foot pedal 105, as well as any other well known mode switching techniques.

FIGS. 3-4 respectively illustrate, as examples, top and right side views of a distal end of the entry guide 200 with the camera 211 and surgical tools 231, 241 extending outward. As shown in a perspective view of a simplified (not to scale) entry guide 200 in FIG. 5, the entry guide 200 is generally cylindrical in shape and has a longitudinal axis X' running centrally along its length. The pivot point, which is also referred to as a remote center "RC", serves as an origin for both a fixed reference frame having X, Y and Z axes as shown and an entry guide reference frame having X', Y' and Z' axes as shown. When the system 100 is in the entry guide positioning mode, the entry guide manipulator 202 is capable of pivoting the entry guide 200 in response to movement of one or more associated input devices about the Z axis (which remains fixed in space) at the remote center "RC" in yaw Ψ. In addition, the entry guide manipulator 202 is capable of pivoting the entry guide 200 in response to movement of the one or more input devices about the Y' axis (which is orthogonal to the longitudinal axis X' of the entry guide 200) in pitch θ, capable of rotating the entry guide 200 about its longitudinal axis X' in roll Φ, and linearly moving the entry guide 200 along its longitudinal axis X' in insertion/retraction or in/out "I/O" directions in response to movement of the one or more associated input devices. Note that unlike the Z-axis which is fixed in space, the X' and Y' axes move with the entry guide 200.

Figure 7:
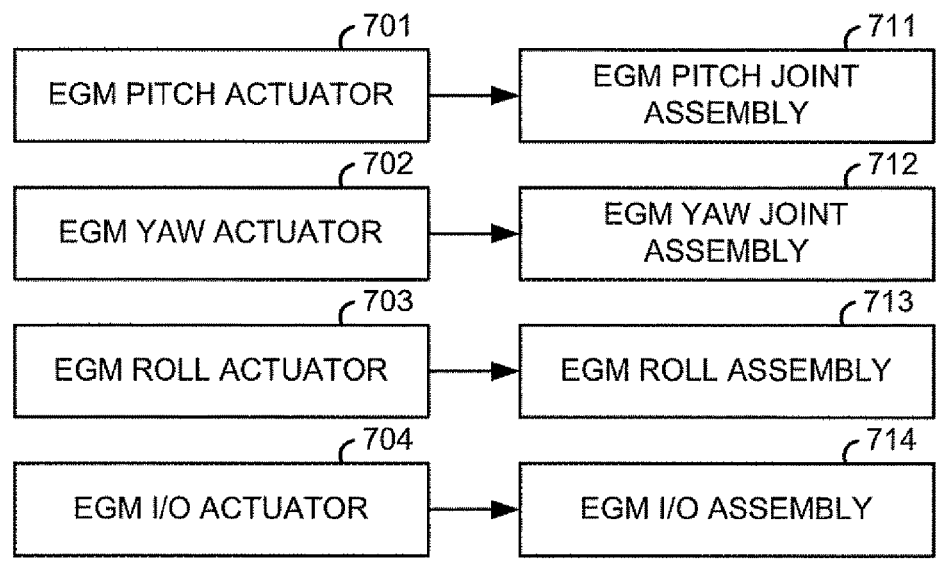
FIG. 7 illustrates a block diagram of interacting components of an entry guide manipulator as used in a medical robotic system utilizing aspects of the present invention.

As shown in FIG. 7, the entry guide manipulator (EGM) 202 has four actuators 701-704 for actuating the four degrees-of-freedom movement of the entry guide 200 (i.e., pitch θ, yaw Ψ, roll Φ, and in/out I/O) and four corresponding assemblies 711-714 to implement them.

Referring back to FIGS. 3-4, the articulatable camera 211 extends through passage 321 and the articulatable surgical tools 231, 241 respectively extend through passages 431, 441 of the entry guide 200. The camera 211 includes a tip 311 (which houses a stereo camera connected to a camera controller and a fiber-optic cable connected to an external light source), first, second, and third links 322, 324, 326, first and second joint assemblies (also referred to herein simply as "joints") 323, 325, and a wrist assembly 327. The first joint assembly 323 couples the first and second links 322, 324 and the second joint assembly 325 couples the second and third links 324, 326 so that the second link 324 may pivot about the first joint assembly 323 in pitch and yaw while the first and third links 322, 326 remain parallel to each other.

The first and second joints 323, 325 are referred to as "joggle joints", because they cooperatively operate together so that as the second link 324 pivots about the first joint 323 in pitch and/or yaw, the third link 326 pivots about the second joint 325 in a complementary fashion so that the first and third links 322, 326 always remain parallel to each other. The first link 322 may also rotate around its longitudinal axis in roll as well as move in and out (e.g., insertion towards the work site and retraction from the worksite) through the passage 321. The wrist assembly 327 also has pitch and yaw angular movement capability so that the camera's tip 311 may be oriented up or down and to the right or left, and combinations thereof.

The joints and links of the tools 231, 241 are similar in construction and operation to those of the camera 211. In particular, the tool 231 includes an end effector 331 (having jaws 338, 339), first, second, and third links 332, 334, 336, first and second joint assemblies 333, 335, and a wrist assembly 337 that are driven by actuators such as described in reference to FIG. 8 (plus an additional actuator for actuating the end effector 331). Likewise, the tool 241 includes an end effector 341 (having jaws 348, 349), first, second, and third links 342, 344, 346, first and second joint assemblies 343,345, and a wrist assembly 347 that are also driven by actuators such as described in reference to FIG. 8 (plus an additional actuator for actuating the end effector 341).

Figure 8:
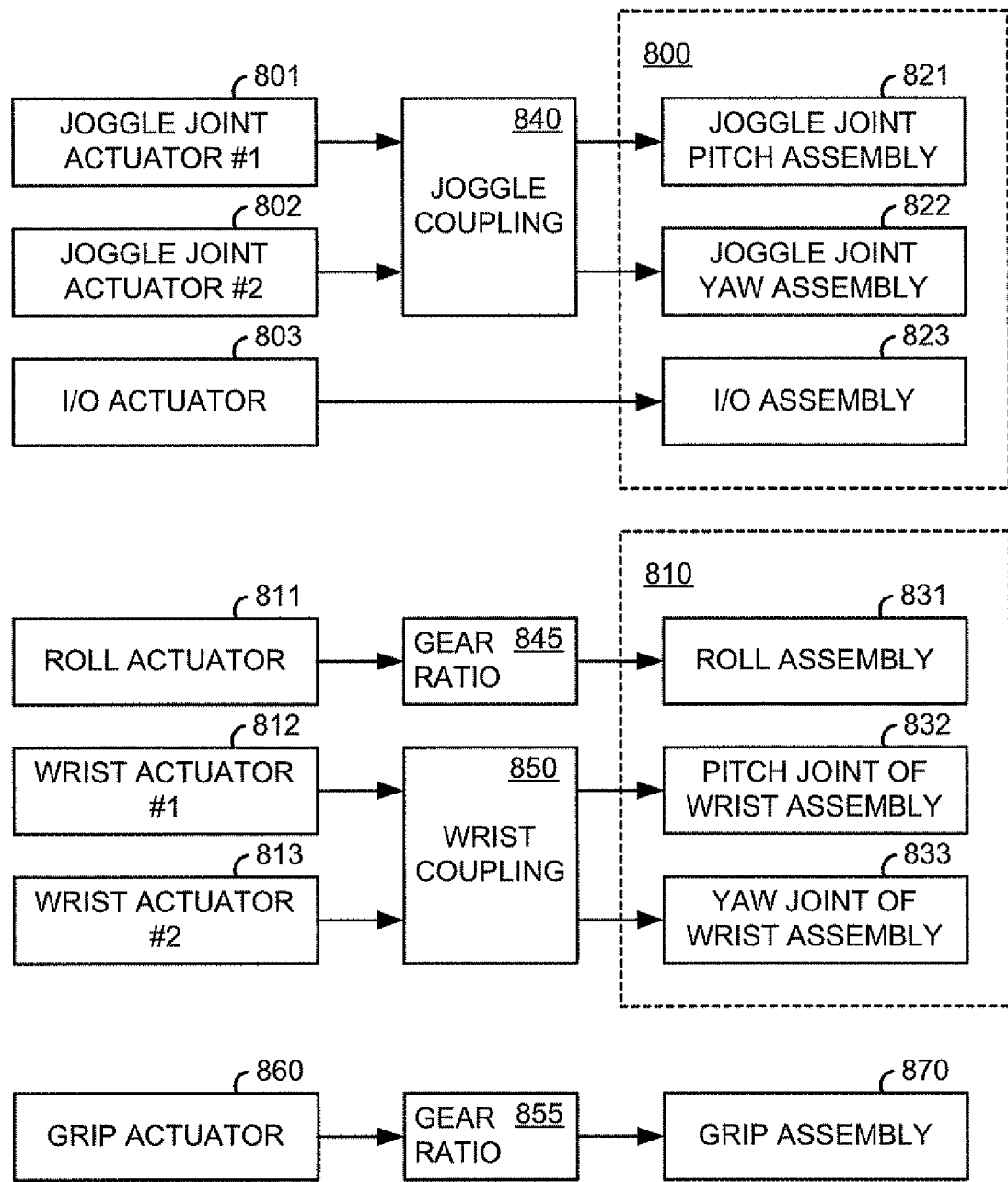
FIG. 8 illustrates a block diagram of interacting components of an articulatable instrument manipulator and an articulatable instrument as used in a medical robotic system utilizing aspects of the present invention.

FIG. 8 illustrates, as an example, a diagram of interacting parts of an articulatable instrument (such as the articulatable camera 211 and the articulatable surgical tools 231, 241) and its corresponding instrument manipulator (such as the camera manipulator 212 and the tool manipulators 232, 242). Each of the instruments includes a number of actuatable assemblies 821-823, 831-833, 870 for effectuating articulation of the instrument (including its end effector), and its corresponding manipulator includes a number of actuators 801-803, 811-813, 860 for actuating the actuatable assemblies.

In addition, a number of interface mechanisms may also be provided. For example, pitch/yaw coupling mechanisms 840, 850 (respectively for the joggle joint pitch/yaw and the wrist pitch/yaw) and gear ratios 845, 855 (respectively for the instrument roll and the end effector actuation) are provided in a sterile manipulator/instrument interface to achieve the required range of motion of the instrument joints in instrument joint space while both satisfying compactness constraints in the manipulator actuator space and preserving accurate transmissions of motion across the interface. Although shown as a single block 840, the coupling between the joggle joint actuators 801, 802 (differentiated as #1 and #2) and joggle joint pitch/yaw assemblies 821, 822 may include a pair of coupling mechanisms—one on each side of the sterile interface (i.e., one on the manipulator side of the interface and one on the instrument side of the interface). Likewise, although shown as a single block 850, the coupling between the wrist actuators 812, 813 (differentiated as #1 and #2) and wrist pitch/yaw joint assemblies 832, 833 may also comprise a pair of coupling mechanisms—one on each side of the sterile interface.

Both the joggle joint pitch assembly 821 and the joggle joint yaw assembly 822 share the first, second and third links (e.g., links 322, 324, 326 of the articulatable camera 211) and the first and second joints (e.g., joints 322, 325 of the articulatable camera 211). In addition to these shared components, the joggle joint pitch and yaw assemblies 821, 822 also include mechanical couplings that couple the first and second joints (through joggle coupling 840) to the joggle joint pitch and yaw actuators 801, 802 so that the second link may controllably pivot about a line passing through the first joint and along an axis that is latitudinal to the longitudinal axis of the first link (e.g., link 322 of the articulatable camera 211) and the second link may controllably pivot about a line passing through the first joint and along an axis that is orthogonal to both the latitudinal and longitudinal axes of the first link.

The in/out (I/O) assembly 823 includes the first link (e.g., link 322 of the articulatable camera 211) and interfaces through a drive train coupling the in/out (I/O) actuator 803 to the first link so that the first link is controllably moved linearly along its longitudinal axis by actuation of the I/O actuator 803. The roll assembly 831 includes the first link and interfaces through one or more gears (i.e., having the gear ratio 845) that couple a rotating element of the roll actuator 811 (such as a rotor of a motor) to the first link so that the first link is controllably rotated about its longitudinal axis by actuation of the roll actuator 811.

The instrument manipulator (e.g., camera manipulator 212) includes wrist actuators 812, 813 that actuate through wrist coupling 850 pitch and yaw joints 832, 833 of the wrist assembly (e.g., wrist assembly 327 of the articulatable camera 211) so as to cause the instrument tip (e.g., camera tip 311) to controllably pivot in an up-down (i.e., pitch) and side-to-side (i.e., yaw) directions relative to the wrist assembly. The grip assembly 870 includes the end effector (e.g., end effector 331 of the surgical tool 231) and interfaces through one or more gears (i.e., having the gear ratio 855) that couple the grip actuator 860 to the end effector so as to controllably actuate the end effector.

Figure 9:
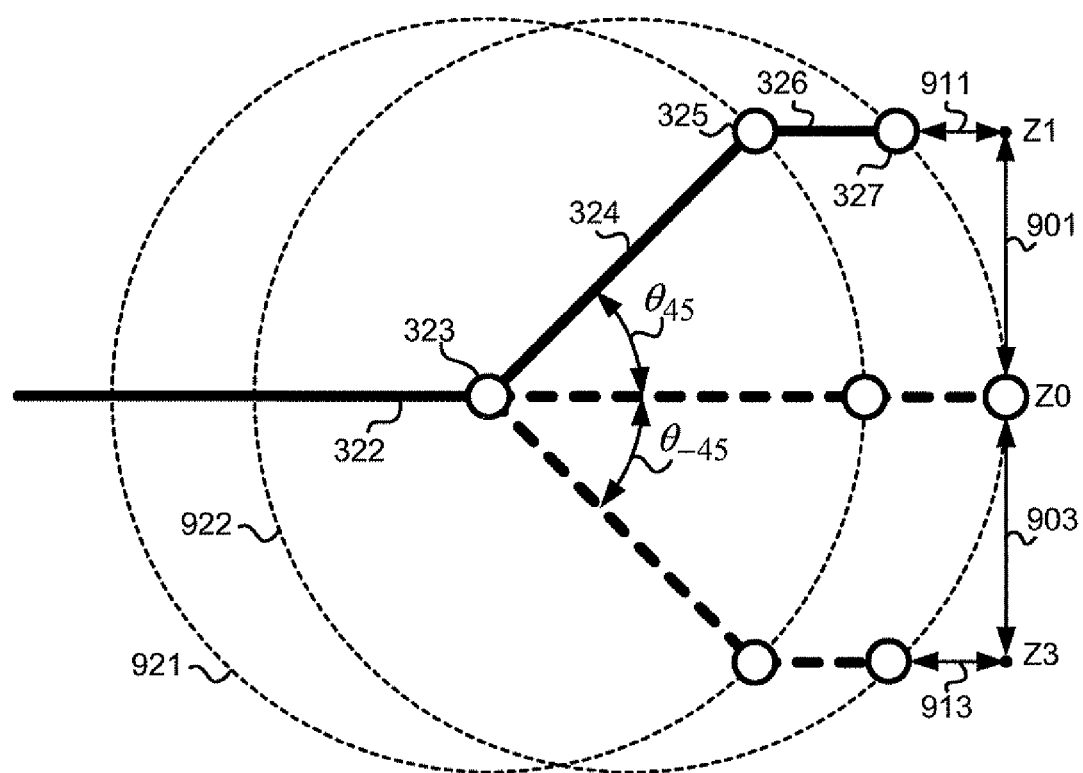
FIG. 9 illustrates a schematic kinematic diagram including a camera joggle-joint pitch assembly with indications of arc compensation for translating its movement to a translational mode movement, as used in a medical robotic system utilizing aspects of the present invention.

The group of instrument joints 800 is referred to as "translational joints" because by actuation of a combination of these joints, the instrument's wrist assembly may be positioned translationally within three-dimensional space. For example, FIG. 9 illustrates a schematic kinematic diagram of the links 322, 324, 326 and joints 323, 325 of the joggle joint pitch assembly 821 of the articulatable camera 211 at three pitch angles, θ=+45, θ=0, θ=−45 degrees, with indications of corresponding arc compensation by the in/out assembly 823 so as to result in translational movement of the wrist assembly 327 in a first direction (vertical in the figure) which is orthogonal to the longitudinal axis (horizontal in the figure) of the first link 322. An indication of the longitudinal axis 401 of the first link 322 and the pitch angle 402 are shown in FIG. 4. If the camera tip 311 is in a fixed orientation relative to the wrist assembly 327 during the translational movement, then the camera tip 311 will also move in an arc corresponding to that of the wrist assembly 327 offset by a fixed length dependent upon the angle of orientation.

In this example, when the links 322, 324, 326 are fully extended outward so that the pitch angle is 0 degrees and the wrist assembly 327 is at a point Z0, no arc compensation is necessary by the in/out assembly 823 if the wrist assembly 327 is to be moved in a vertical direction along a line passing through the point Z0. On the other hand, when the second link 324 is rotated +45 degrees in pitch at the first joint 323 about a first axis which is orthogonal to the longitudinal axis 401 of the link 322, the position of the wrist assembly 327 relative to the first joint 323 has a tangential component 901. In order for the movement of the wrist assembly 327 to move in the vertical direction along the line passing through the point Z0, however, the in/out assembly 823 must move the wrist assembly 327 forward (i.e., in) to the point Z1 by a distance indicated as 911. Similarly, if the second link 324 is rotated −45 degrees in pitch at the first joint 323 about the first axis, the position of the wrist assembly 327 relative to the first joint 323 has a tangential component 903 and the in/out assembly 823 must move the wrist assembly 327 forward to a point Z3 by a distance indicated as 913 in order for the movement of the wrist assembly 327 to move along the vertical line passing through the point Z0. For other angles of pitch rotation, the second joint 325 moves along a circle 921 having a radius equal to the length of the second link 324, the wrist assembly 327 moves along a corresponding circle 922 of equal radius that is offset from the circle 921 by an amount equal to the length of the third link 326 along the longitudinal axis of the first link 322, and the arc compensation required by the in/out assembly 823 is the distance from the wrist assembly 327 to the vertical line passing through the point Z0.

The joggle joint yaw assembly 822 operates in a similar manner as the joggle joint pitch assembly 821. Except that in this case, the second link 324 is rotated at the first joint 323 about a second axis which is orthogonal to both the first axis (as used by the pitch assembly 821) and the longitudinal axis 401 of the link 322.

When the joggle joint pitch and yaw assemblies 821, 822 are actuated concurrently, such as through joggle coupling 840, the resulting movement of the wrist assembly 327 may follow a portion of a sphere (i.e., a three-dimensional version of the circle 922). In this case, if the movement of the wrist assembly 327 is to be on a plane passing through and perpendicular to the longitudinal axis of the link 322, then the compensation required by the in/out assembly 823 is the distance from the wrist assembly 327 to the plane.

Note that in the above example, it is assumed that both the joggle joint pitch and yaw assemblies 821, 822 pivot the second link 324 about the same pivot point. In practicing the invention, however, they may pivot about slightly different pivot points if the first and second joints 323, 325 are first and second joint assemblies in which each joint assembly includes a pitch joint, a yaw joint and a short link separating and coupling the pitch and yaw joints. In this case, first and second pitch joints respectively of the first and second joint assemblies 323, 325 are coupled together as part of the joggle joint pitch assembly 821, and first and second yaw joints respectively of the first and second joint assemblies 323, 325 are coupled together as part of the joggle joint yaw assembly 822. First and second short links of the first and second joint assemblies 323, 325 are referred to as being short, because they are each shorter than the first link 322, second link 324 and third link 326. The first and second short links are also constrained to be parallel to each other at all times, like the first and third links 322, 326. In addition, as may be readily appreciated in light of the geometries of the first and second joint assemblies 323, 325, rather than moving along the surface of a sphere, the wrist assembly 327 may follow a different concave virtual surface when both the joggle joint pitch and yaw assemblies 821, 822 are actuated at the same time.

Figure 10:
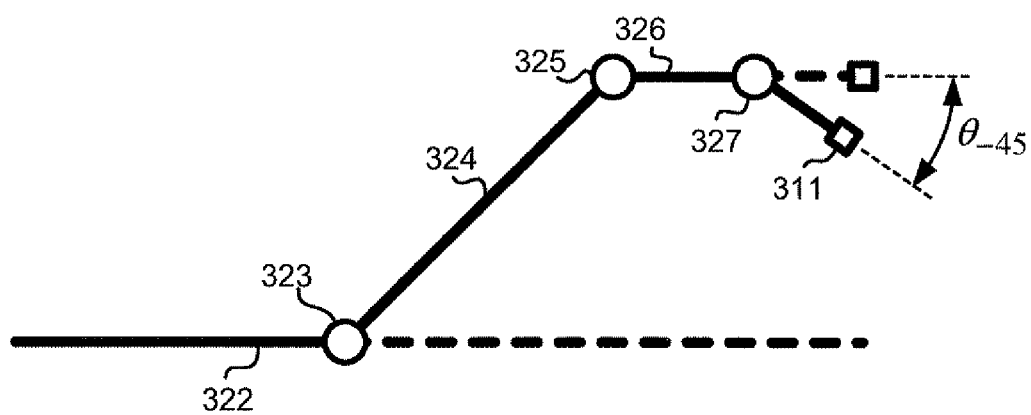
FIG. 10 illustrates a schematic kinematic diagram including a camera wrist assembly for providing orientational mode movement, as used in a medical robotic system utilizing aspects of the present invention.

The group of instrument joints 810 is referred to as "orientational joints" because by actuation of these joints, the instrument's tip may be oriented about the wrist assembly. For example, FIG. 10 illustrates a schematic kinematic diagram including the wrist assembly 327 as it pivots the camera's tip 311 about its pitch joint 832 to a −45 degrees pitch angle while the links 322, 324, 326 and joints 323, 325 of the camera instrument's joggle-joint pitch assembly 821 are controllably held in place. The wrist assembly 327 may also pivot the camera's tip 311 about its yaw joint 833 in a similar manner. When the camera's tip 311 is pivoted about both the pitch and yaw joints 832, 833 concurrently by operation of the wrist assembly 327, such as through wrist coupling 850, the resulting movement of the camera tip 311 may follow a concave virtual surface. However, if the pitch and yaw joints 832, 833 are the same joint, such as a ball joint, then the resulting movement of the camera tip 311 may follow a portion of a sphere.

Figure 11:
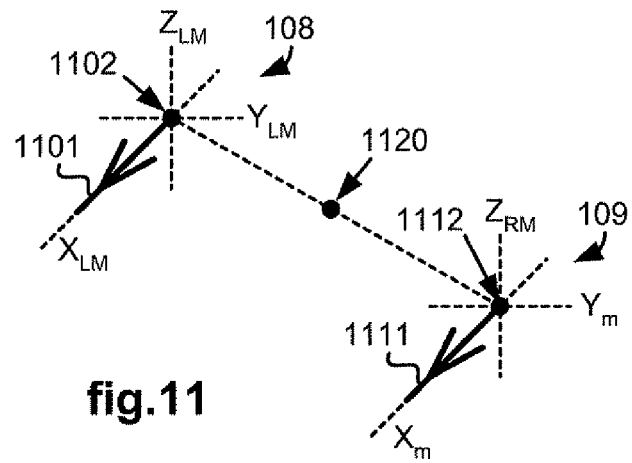
FIG. 11 illustrates reference frames for left and right input devices and a set-point defined between the input devices, as used in a medical robotic system utilizing aspects of the present invention.

FIG. 11 illustrates, as an example, reference frames for the input devices 108, 109. In particular, Cartesian coordinate system $X_{LM}$, $Y_{LM}$, $Z_{LM}$ defines a first reference frame associated with the left-hand input device 108 and Cartesian coordinate system $X_{RM}$, $Y_{RM}$, $Z_{RM}$ defines a second reference frame associated with the right-hand input device 109.

The left-hand input device 108 provides three translational degrees-of-freedom movement (i.e., forward/back along the longitudinal axis $X_{LM}$ of a gripper 1101 of the input device 108, side-to-side along a first axis $Y_{LM}$ orthogonal to the longitudinal axis $X_{LM}$, and up/down along a second axis $Z_{LM}$ orthogonal to both the first axis and the longitudinal axis $X_{LM}$) for a pivot point 1102 of its gripper 1101. The left-hand input device 108 also provides three orientational degrees-of-freedom movement (i.e., roll about the longitudinal axis $X_{LM}$, pitch about the first axis $Y_{LM}$, yaw about the second axis $Z_{LM}$) for the pivot point 1102 of its gripper 1101. In addition, squeezing the gripper 1101 may provide an additional degree-of-freedom for manipulating an end effector of a surgical tool associated with the input device 108 at the time.

The right-hand input device 109 also provides three translational degrees-of-freedom movement and three orientational degrees-of-freedom movement for a pivot point 1112 of its gripper 1111 in a similar manner as the left-hand input device 108 provides for the pivot point 1102 of its gripper 1101. In addition, squeezing the gripper 1111 may also provide an additional degree-of-freedom for manipulating an end effector of a surgical tool associated with the input device 109 at the time.

Thus, each of the input devices 108, 109 is capable of providing at least six degrees-of-freedom movement for controlling an associated device such as one of the surgical tools 231, 241, the articulatable camera 211, and the entry guide 200.

Figure 12:
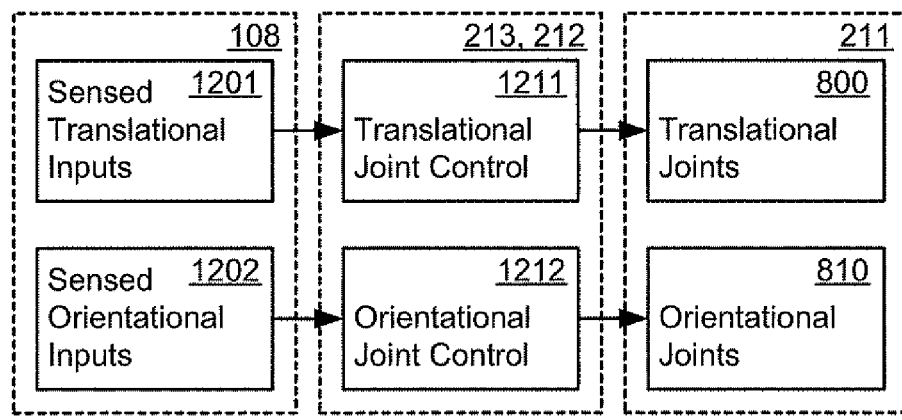
FIG. 12 illustrates a block diagram of a camera instrument control scheme using a single input device for concurrent translational and orientational mode control, as used in a medical robotic system utilizing aspects of the present invention.

As one example of such single input device control, FIG. 12 illustrates a block diagram in which the input device 108 is associated with and used to control positioning (i.e., translationally and orientationally) of the tip 311 of the camera instrument 211. In this example, operator manipulated movement of the three translational degrees-of-freedom of the input device 108 is sensed and used to command translational movement of the camera's wrist assembly 327 through translational joints 800 of the camera instrument 211, and operator manipulated movement of the three orientational degrees-of-freedom of the input device 108 is sensed and used to command orientational movement of the camera's tip 311 about its wrist assembly 327 through orientational joints 810 of the camera instrument 211. Because of this partitioning of the translational and orientational modes, the operator/Surgeon generally knows which joints of the camera instrument 211 are moving (i.e., the translational joints 800 or the orientational joints 810) when manipulating the input device 108, thus providing an intuitive sense to the operator of the likelihood that the links of the camera instrument 211 will collide with the links of one of the surgical tools 231, 241 during the camera positioning process.

The input devices 108, 109 may also be used in tandem to control the camera instrument 211, such as using a virtual handlebar image referenced control technique in which a set-point 1120 midway between pivot points 1102, 1112 of the input devices 108, 109 is used to control movement of the camera instrument 211.

Figure 13:
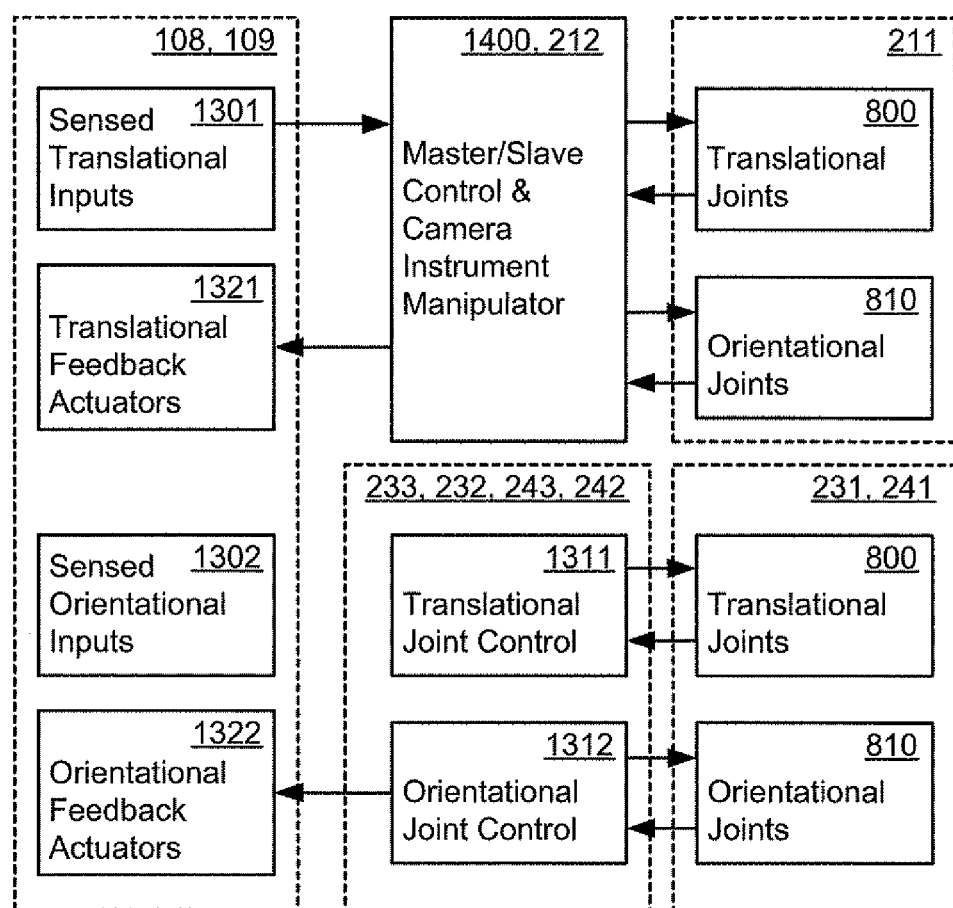
FIG. 13 illustrates a block diagram of a camera instrument control scheme using coupled input devices for non-current translational and orientational mode control while automatically maintaining master/instrument alignment, as used in a medical robotic system utilizing aspects of the present invention.

As one example of such dual input device control, FIG. 13 illustrates a block diagram in which the input devices 108, 109 are associated with and used to control positioning (i.e., translationally and orientationally) of the tip 311 of the camera instrument 211 using a virtual handlebar image referenced control. In this example, operator manipulated movement of the three orientational degrees-of-freedom of the virtual handlebar coupled input devices 108, 109 (e.g., as sensed in 1302) is ignored by the master/slave control system 1400 and only the three translational degrees-of-freedom of the input devices 108, 109 (e.g., as sensed in 1301) are used to command both the translational and orientational movements of the camera instrument 211 as described in reference to the control system 1400 of FIG. 14. Meanwhile, orientational feedback actuators 1322 of the input devices 108, 109 receive feedback commands from the orientational joints of their respective surgical tools 231, 241 (even though the input devices 108, 109 have been temporarily disassociated from the surgical tools 231, 241 and associated with the camera instrument 211) so as to maintain the orientational alignments of input devices 108, 109 with their respective surgical tools 231, 241. Thus, realignment of the input devices 108, 109 with their respective surgical tools 231, 241 is not required before reassociating the input devices 108, 109 to the surgical tools 231, 241 after positioning the camera instrument 211.

Figure 14:
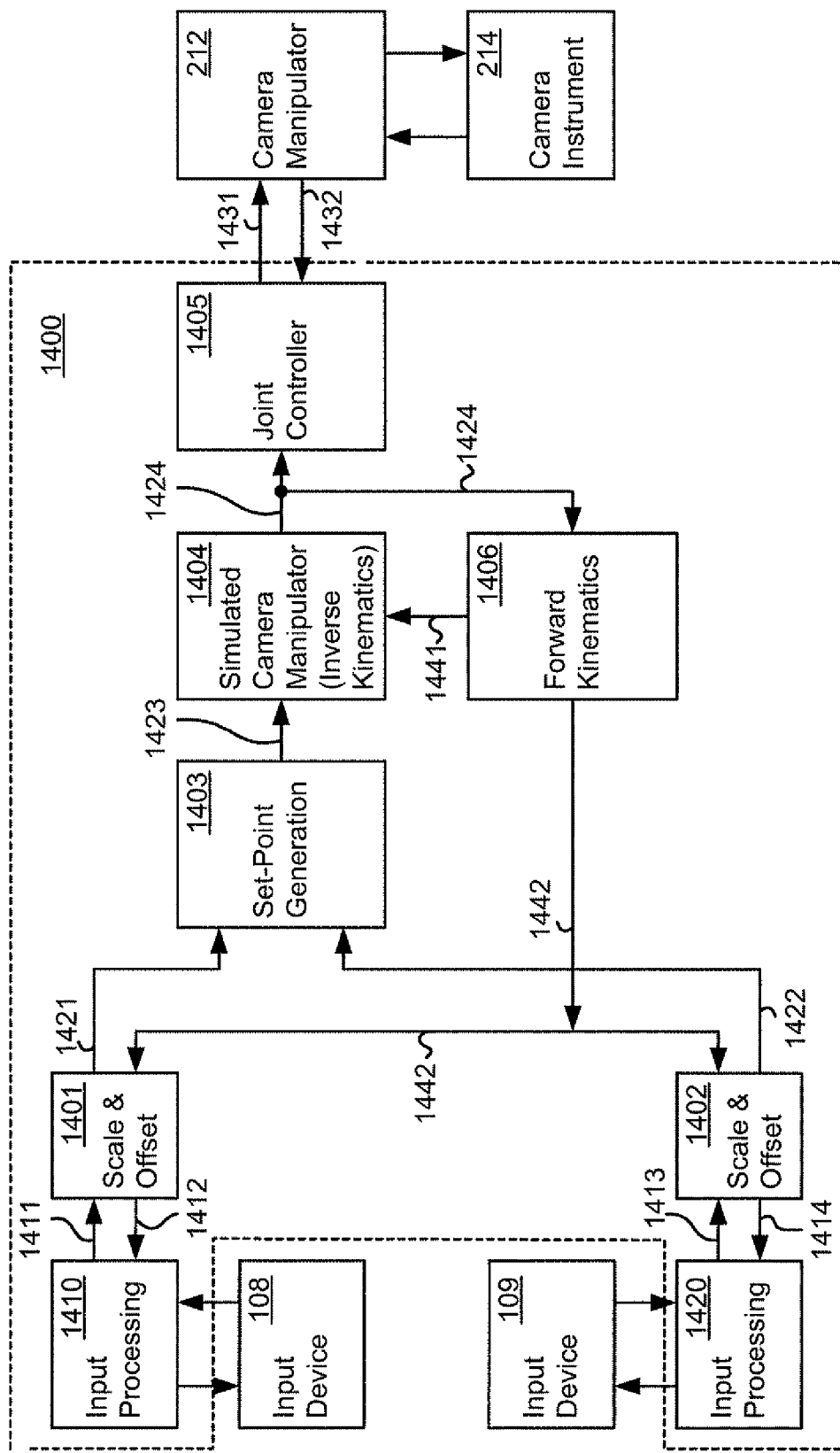
FIG. 14 illustrates a block diagram of a control system for moving a camera according to a method utilizing aspects of the present invention.

FIG. 14 illustrates, as an example, a block diagram of a control system 1400 for controlling positioning (i.e., both translationally and orientationally) of the camera instrument 211 in response to movement of the input devices 108, 109 when the input devices 108, 109 are selectively associated with the camera 211 in their respective camera positioning modes "C2" and "C1". In this example, both input devices 108, 109 are used to position the camera instrument 211 in a virtual handlebar fashion so as to provide the sensation to the Surgeon that he or she is grasping the image being displayed on the monitor 104 with his or her left and right hands and moving the image about the work site to a desired viewing point using image referenced camera control.

The input devices 108, 109 include a number of links connected by joints so as to facilitate multiple degrees-of-freedom movement. For example, as the Surgeon moves the input devices 108, 109 from one position to another, sensors associated with the joints of the input devices 108, 109 sense such movement at sampling intervals (appropriate for the processing speed of the controller 102 and camera control purposes) and provide digital information indicating such sampled movement in joint space to input processing blocks 1410, 1420.

Input processing blocks 1410, 1420 process the information received from the joint sensors of the input devices 108, 109 to transform the information into corresponding desired positions and velocities for the camera 211 in its Cartesian space relative to a reference frame associated with the position of the Surgeon's eyes (the "eye reference frame"), by computing joint velocities from the joint position information and performing the transformation using a Jacobian matrix and eye related information using well-known transformation techniques.

Scale and offset processing blocks 1401, 1402 receive the processed information 1411, 1413 from the input processing blocks 1410, 1420 and apply scale and offset adjustments to the information so that the resulting movement of the camera instrument 211 and consequently, the image being viewed on the monitor 104 appears natural and as expected by the operator of the input devices 108, 109. The scale adjustment is useful where small movements of the camera 211 are desired relative to larger movement of the input devices 108, 109 in order to allow more precise movement of the camera instrument 211 as it views the work site. To implement the shared control for moving the camera instrument 211 by the input devices 108, 109, lateral offsets are applied to shift the control point to the left for the input device 108 which is being operated by the left hand of the operator and to the right for the input device 109 which is being operated by the right hand of the operator. In addition, offset adjustments are applied for aligning the input devices 108, 109 with respect to the Surgeon's eyes as he or she manipulates the input devices 108, 109 to command movement of the camera instrument 211 and consequently, its captured image that is being displayed at the time on the monitor 104.

Moreover, offsets can be used to account for potential asymmetries in the lengths of the surgical tools. When performing different medical procedures, different tool tips might be required for example to retract tissue with the left tool while the right one is equipped with scissors to perform cutting. Even though the proximal portions of the tools are identical, the tips might have substantially different lengths. Therefore the center of the two tips is effectively shifted towards the shorter tool. The control point of the camera can be shifted by the same amount, in order to improve the ability of the surgeon to keep both tools inside the camera field of view. This approach is extendable to also handle the case where more than two tools are being used during the procedure.

The outputs 1421, 1422 of the scale and offset blocks 1401, 1402 are provided to a set-point generation block 1403 so that a single set of position and velocity commands is provided for the camera manipulator 212. Therefore, as the operator moves the input devices 108, 109, he or she forces a motion on the mid-point (i.e., set-point) of what feels like to the operator to be a "virtual handlebar". This motion is then "transferred" to subsequent blocks of the control system 1400 as a set-point for Cartesian motions.

Although each of the input devices 108, 109 has six Cartesian degrees of freedom (i.e., three for position and three for orientation), by coupling the two input devices 108, 109 together, three constraints are introduced since the resulting "virtual handlebar" relates together the (x, y, z) Cartesian positions of the two input devices 108, 109. Thus, instead of twelve degrees of freedom being available for the two input devices 108, 109, only nine degrees of freedom remain available to compute the Cartesian set-point for the camera instrument 211. Since only a six degree of freedom Cartesian set-point is necessary to drive a generic (steerable) camera instrument, the available nine degrees of freedom are normally adequate.

However, since the input devices 108, 109 are shared so that they are also used to control the tools 231, 241, after the Surgeon positions the camera 211 to a new viewing point, the input devices 108, 109 are re-associated with the tools 231, 241 so the Surgeon may proceed to perform a medical procedure. Prior to making the switch, it is necessary to realign the tools 231, 241 with the input devices 108, 109.

One way to avoid having the Surgeon re-align the input devices 108, 109 before switching back to their respective tool following modes "T2" and "T1" is to control the orientations of the input devices 108, 109 in such a way that they remain aligned with the tools 231, 241 as the camera instrument 211 moves during the camera repositioning mode. With this constraint, however, the available number of degrees of freedom drops to only three since three degrees of freedom of orientation are used for each of the input devices 108, 109.

Thus, one aspect of the present invention is to break up camera movement into orientational and translational modes (one performed after the other) so that a full six degree of freedom movement is provided albeit with only three degrees of freedom available at a time. As previously explained in reference to FIG. 8, in the translational mode, actuators 801-803 may be operated in combination to provide translational movement of the wrist assembly 327 in response to the movement of the constrained input devices 108, 109 while the pitch and yaw joints of the wrist assembly 327 and the roll assembly 831 are locked. Also, in the orientational mode, actuators 812, 813 may be operated to provide orientational movement of the wrist assembly 327 in response to the movement of the input devices 108, 109 while the pitch and yaw joints of the wrist assembly 327 (acting as a pivot) are locked in space. Although the roll assembly 831 is designated as one of the orientational joints 810, it is not generally activated in this implementation without concurrently activating the translational joints 800, because its activation may result in moving the wrist assembly 327 if compensating movement of the translational joints 800 is not concurrently performed (except for the limited case where the camera instrument 211 is in its fully extended position as indicated by wrist assembly 327 being at point Z0 in FIG. 9).

In orientational mode, Z and Y translational movements of the input devices 108, 109 are respectively translated into pitch and yaw movements of the wrist assembly 327, up to predefined threshold values which may be magnitude or velocity related. X translational movement of the input devices 108, 109, on the other hand, is ignored up to a predefined threshold value which also may be magnitude or velocity related. When any of the X, Y or Z translational movements exceeds its respective threshold value, then a release condition is met (like a detent) in which further movement in that direction causes a mode switch to translational mode.

Figure 15:
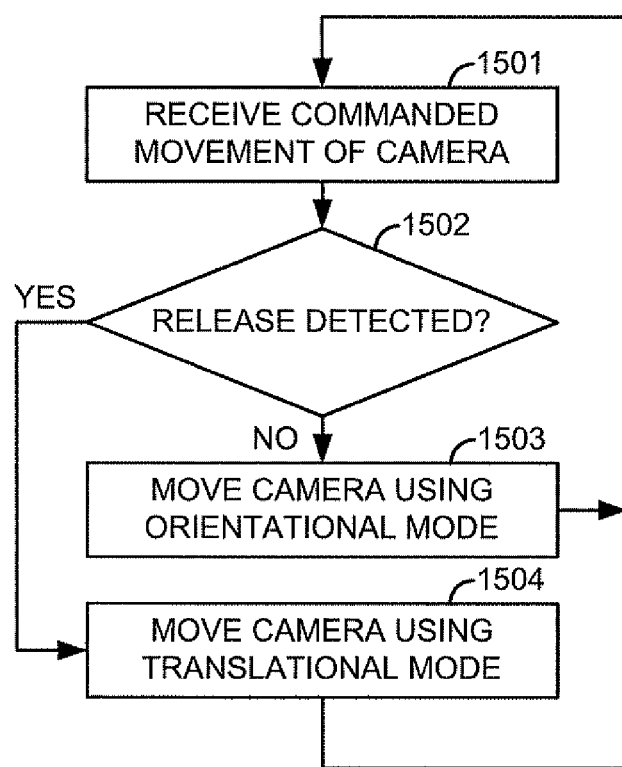
FIG. 15 illustrates a flow diagram of a method for moving a camera in response to a movement of an input device of a medical robotic system, utilizing aspects of the present invention.

A simulated camera block 1404 receives the output 1423 of the set-point generation block 1403 and transforms the commanded position and velocity for the camera 211 from the Cartesian space to its joint space using its inverse kinematics while avoiding singularities in its operation, limiting the commanded joint positions and velocities to avoid physical limitations or other constraints such as avoiding harmful contact with tissue or other parts of the Patient, and applying virtual constraints on the joints such as those required to implement a method for moving (or positioning) the camera instrument 211 as described in reference to FIG. 15 and various versions of the method or alternative methods as described in reference to FIGS. 16-19. Avoidance of singularities may be performed using a modified Jacobian inverse controller and joint position and velocity limits may be imposed such as described in U.S. Pat. No. 6,671,581 "Camera Referenced Control in a Minimally Invasive Surgical Apparatus," which has been incorporated herein by reference.

The output 1424 of the simulated camera block 1404 is then provided to a joint controller block 1405 and a forward kinematics block 1406. The joint controller block 1405 includes a joint control system for each controlled joint (or operatively coupled joints such as "joggle joints") of the camera instrument 211. The output 1424 of the simulated camera block 1404 provides the commanded value for each joint of the camera instrument 211. For feedback control purposes, sensors associated with each of the controlled joints of the camera instrument 211 provide sensor data 1432 back to the joint controller block 1405 indicating the current position and/or velocity of each joint of the camera instrument 211. The sensors may sense this joint information either directly (e.g., from the joint on the camera instrument 211) or indirectly (e.g., from the actuator in the camera manipulator 212 driving the joint). Each joint control system in the joint controller 1405 then generates torque commands for its respective actuator in the camera manipulator 212 so as to drive the difference between the commanded and sensed joint values to zero in a conventional feedback control system manner.

The forward kinematics block 1406 transforms the output 1424 of the simulated camera block 1404 from joint space back to Cartesian space relative to the eye reference frame using the forward kinematics of the camera instrument 211. The scale and offset blocks 1401, 1402 perform an inverse scale and offset functions on the output 1442 of the forward kinematics block 1406 (as well as performing a reversal of the set-point generation) before passing their respective outputs 1412, 1414 to the input processing blocks 1410, 1420 where error values are calculated between their respective outputs 1411, 1413 and inputs 1412, 1414. If no limitation or other constraint had been imposed on the input 1423 to the simulated camera block 1404, then the calculated error values would be zero. On the other hand, if a limitation or constraint had been imposed, then the error value is not zero and it is converted to a torque command that drives actuators in the input devices 108, 109 to provide force feedback felt by the hands of their operator. Thus, the operator becomes aware that a limitation or constraint is being imposed by the force that he or she feels resisting his movement of the input devices 108, 109 in that direction. In addition to this force feedback, forces coming from other sensors or algorithms (e.g., a force/pressure sensor or an algorithm to avoid the work volume of the surgical tools to prevent collisions) may be superimposed on the force feedback.

An output 1441 of the forward kinematics block 1406 may also be provided to the simulated camera block 1404 for control purposes. For example, the simulated position output may be fed back and compared with the commanded position.

For single input device control of the camera instrument 211, such as described in reference to FIG. 12, the control system 1400 may be modified in a straightforward manner. For example, the set-point generation block 1403 may be eliminated in that case since the control point would simply be the pivot point of the input device (e.g., 1102 for the input device 108). Although the camera instrument 211 may still be positioned using image referenced control, it may or may not use the automatic alignment technique described in reference to FIG. 13, and consequently, it may or may not place restrictions on the concurrent operation of the translational and orientational modes.

FIG. 15 illustrates, as an example, a flow diagram of a method (preferably implemented in the simulated camera block 1404 of the control system 1400 of FIG. 14) for moving the camera instrument 211 in response to movement of an input device (e.g., one or both of input devices 108, 109) of the medical robotic system 100 while the distal end of the entry guide 200 (including the camera instrument 211 and surgical tools 231, 241 extending out thereof) is positioned within the Patient to perform a medical procedure on the Patient at the work site.

In 1501, the method starts by receiving the commanded movement of the camera instrument 211. The commanded movement in this case may be received after the avoidance of singularities and physical joint limitations have been performed, such as described in reference to block 1404 of FIG. 14.

In 1502, a determination is made whether a release has been detected. The release is preferably indicated by the operator of the input device through operator interaction with the medical robotic system 100 such as when the operator exerts a force on the input device that exceeds a threshold value, or when the operator moves the input device at a velocity that exceeds a threshold value, or when the operator moves the input device a distance or magnitude that exceeds a threshold value. Other ways that the operator may interact with the medical robotic system 100 to indicate a release is by depressing a button or switch on the input device (e.g., on one of the input devices 108, 109), or depressing the foot pedal 105, or providing an appropriate input to the graphical user interface 170, or providing an appropriate voice command to the voice recognition system 160. When two input devices are used to control movement of the camera instrument 211, movement of the input devices relative to each other may also be used to indicate a release.

If a release is not detected in 1502 (i.e., the determination is NO), then in 1503, the method moves the camera instrument 211 using an orientational mode in which it constrains the movement of the camera instrument 211 so that its focal point moves along a concave virtual surface. This mode provides a natural feel to the Surgeon since it results in the image (that is being viewed by the Surgeon on the monitor 104) moving in a similar fashion as the view that the Surgeon's eyes would see as he or she turns his or her head to the left or right or up or down. The orientational mode may be accomplished, for example, by actuating at least one actuator of the camera manipulator 212 (e.g., one or both of the actuators 812, 813 described in reference to FIG. 8) in response to the movement of the input device so that the tip 311 of the camera instrument 211 is rotated about a pivot (e.g., the wrist pitch and/or yaw joints 832, 833) of the camera 211. Preferably, the actuators 801-803 (which are used for the translational mode) are locked during orientational mode so that the pivot does not move (i.e., there is no translational movement of the pivot during the orientational mode). The roll actuator 811 may also be locked during this time since its operation is not necessary for controlled orientational movement of the camera tip 311 and further, as previously described, its operation may require concurrent actuation of the translational actuators 801-803 which are locked at this time.

On the other hand, if the release is detected in 902 (i.e., the determination is YES), then in 904, the method proceeds by allowing translational movement of the camera instrument 211 in a three-dimensional space (e.g., a volume defined in an appropriate reference frame). Since translational movement of the camera instrument 211 is not allowed until a release is detected, collisions with the links of the surgical tools being used to perform the medical procedure are likely avoided during the period before detection of the release and consequently, collisions between the camera and tool instruments are likely avoided during that period. This translational mode may be accomplished, for example, by allowing actuation of a plurality of actuators of the camera manipulator 212 (e.g., two or more of the actuators 801-803) in response to the movement of the input device so that the pivot (e.g., wrist pitch and yaw joints 832, 833) of the camera instrument 211 is positionable in the three-dimensional space. Preferably, the actuators 811-813 (which are used for the orientational mode), are locked during translational mode so that the orientation of the tip 311 of the camera instrument 211 does not move during the translational mode.

After performing either 1503 or 1504, the method loops back to 1501 to process the next commanded movement of the camera instrument 211, which corresponds to the position and velocity of the input device sampled at the next process cycle.

Ideally, the concave virtual surface that the focal point of the camera instrument 211 is constrained to move along in 1503 is a surface of a sphere centered at the lens (e.g., distal ends of the fiber optic pair) of the camera 211 so that the Surgeon gets the impression viewing the monitor 104 that the image is exactly rotating about the Surgeon's eyes. In the present implementation, however, the pivot point is chosen to be the wrist pitch and yaw joints 832, 833 and as a consequence, certain tradeoffs from the ideal are accepted for practical reasons. For example, the wrist pitch and yaw joints 832, 833 may not result in a constraining surface that is exactly spherical, because they may be two different rotary joints offset by a finite distance rather than a single universal or ball joint. Also, even though the joggle-joint construction used in the camera instrument 211 helps to substantially reduce the necessary distance between the wrist assembly 327 and the camera tip 311, the distance is still non-negligible. These trade-offs are justifiable, however, because to provide the Surgeon with the experience of the ideal case, extensive image processing may be required that is both process intensive and time consuming, while at the same time, may not even provide the Surgeon with an appreciably noticeable enhanced experience.

Also, although it is the focal point of the camera instrument 211 that is described as being constrained in 903, it is to be appreciated that for computational purposes (i.e., use in the control algorithm), the constraining surface does not have to be at a distance corresponding to the focal point of the camera instrument 211. A different constraining surface at a different working distance may be used. In particular, the working distance "d" which affects the radius and curvature of the concave virtual surface may be another length based upon the following considerations. A value of "d" that is larger than the focal point distance results in a larger radius and consequently, a smoother motion due to its lower angular velocity for a given movement of the input devices 108, 109. On the other hand, a value of "d" that is smaller than the focal point distance results in more responsive behavior that uses less workspace (i.e., less movement) at the input device side. As one benefit of using a different "d" value than the focal point length, the neutral position of the camera instrument 211 may be slightly offset so that the surgical tool instruments 231, 241, which might have substantially different lengths, appear centered in the image captured by the camera instrument 211 and presented to the Surgeon on the monitor 104.

Figure 16:
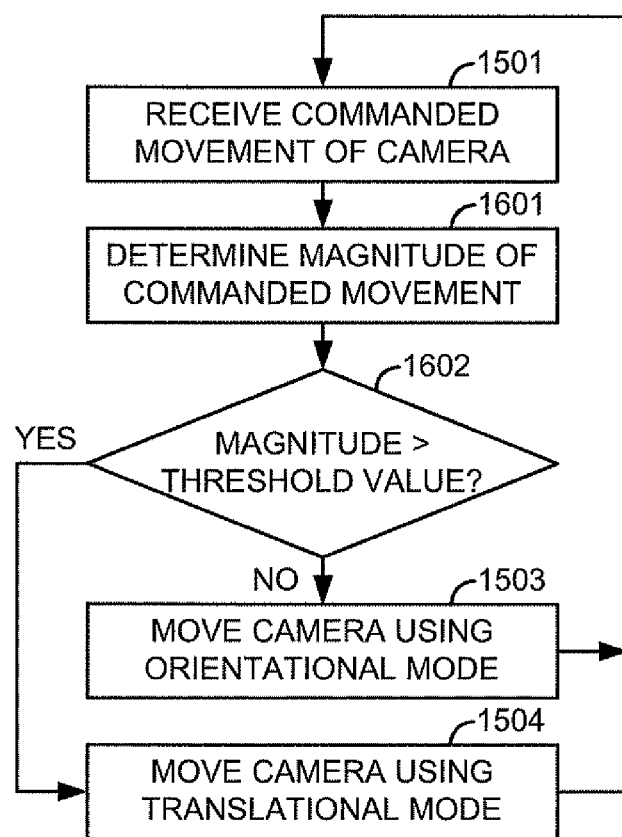
FIG. 16 illustrates a flow diagram of one version of the method for moving a camera in response to a movement of an input device of a medical robotic system, utilizing aspects of the present invention.

FIG. 16 illustrates, as an example, a flow diagram of one version of the method described in reference to FIG. 15 in which the detection of the release in 1502 is performed by 1601 and 1602, wherein in 1601, the magnitude of the commanded movement of the camera instrument 211 is determined and in 1602, the release is determined to have occurred if the magnitude is greater than a threshold value. The magnitude in this example may be incremental or absolute. Other tasks referenced as 1501, 1503, 1504 are performed in the same manner as their like referenced counterparts in the method of FIG. 15.

In the methods described in reference to FIGS. 15, 16, the orientational and translational modes are mutually exclusive (i.e., either one or the other is performed, but not both at the same time) and the transition between the two modes is a discrete event that requires an explicit user input (i.e. pressing a foot pedal, etc.).

Figure 17:
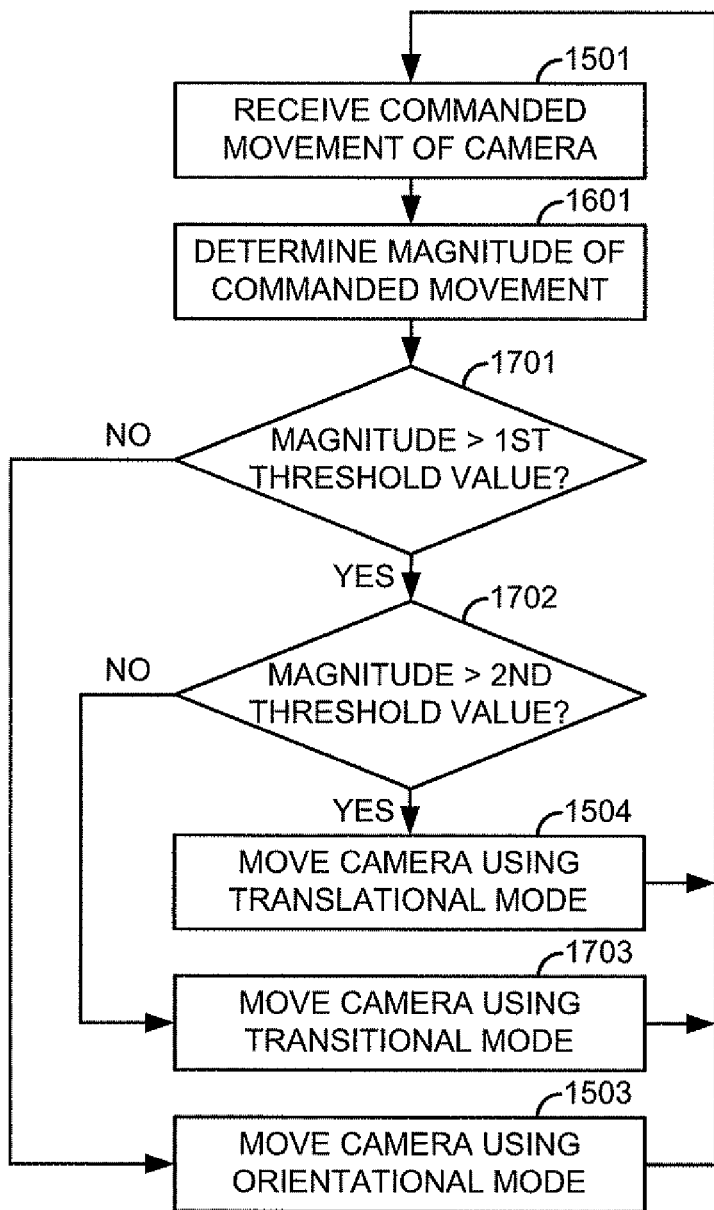
FIG. 17 illustrates a flow diagram of an alternative method for moving a camera in response to a movement of an input device of a medical robotic system, utilizing aspects of the present invention.

FIG. 17 illustrates, as an example, a flow diagram of an extension to the method described in reference to FIG. 16, in which a transitional mode is added in which both orientational and translational modes are allowed to be active at the same time. In this method, after determining the magnitude of the commanded movement in 1601 (in the same manner as its like-referenced counterpart in the method of FIG. 16), a determination is made in 1601 whether the magnitude is greater than a first threshold value. If the determination in 1701 is NO, then the method operates in the orientational mode in 1503 (i.e., in the same manner as its like-referenced counterpart in the method of FIG. 15). On the other hand, if the determination in 1701 is YES, then in 1702, a determination is made whether the magnitude is greater than a second threshold value (which is greater than the first threshold value). If the determination in 1702 is YES, then the method operates in the translational mode in 1504 (i.e., in the same manner as its like-referenced counterpart in the method of FIG. 15). On the other hand, if the determination in 1702 is NO, then in 1703, the method operates in the transitional mode. In this way the transition between the translational mode and the orientational mode does not require an explicit user input, but happens as an implicit consequence of the motion that the user is commanding at the input devices.

Note that the range of motion in which the transitional mode is operative is determined by the selection of the first and second threshold values. In this regard, if the first and second threshold values are equal, then the method of FIG. 17 would be the same as the method of FIG. 16.

Figure 18:
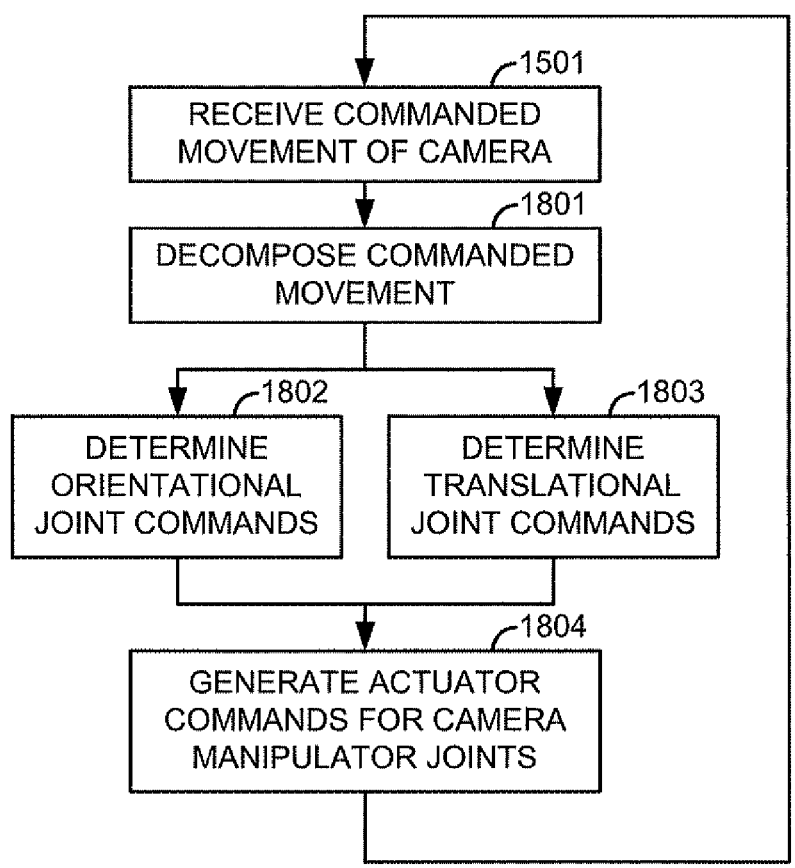
FIG. 18 illustrates a flow diagram of an enhanced version of the alternative method for moving a camera in response to a movement of an input device of a medical robotic system, utilizing aspects of the present invention.

FIG. 18 illustrates, as an example, a flow diagram of another extension of the method of FIG. 15 in which the transition into and out of a transitional mode (in which both orientational and translational modes are concurrently active) is made to be gradual. In this method, after receiving the commanded movement of the camera in 1501 (in the same manner as its like-referenced counterpart in the method of FIG. 15), in 1801, the commanded movement is decomposed into orientational and translational components using, for example, a dynamic filter.

In 1802 and 1803, the joint commands implementing the orientational and translational modes are determined by applying a smoothing function to the orientational and translational components so as to gradually phase out one of the modes while gradually phasing in the other as a function of displacement of the input device or other input related characteristic(s). In other words, the dynamic filter uses the knowledge of the trajectory (time, position and velocity) commanded by the operator in order to properly generate a simultaneous rotational and a translational motion command. For example, the dynamic filter can be implemented in such a way to mimic inertial and viscous characteristics (that will be perceived at the input device by means of force feedback); rapid and small motions of the input device will not move the filter inertia and will be interpreted as orientational commands, while the low frequency content will substantially cause a linear translation of the filter inertia and will be interpreted as translational commands.

In 1804, the actuator commands for the joints of the camera manipulator 212 are generated as the output 1424 of the simulated camera block 1404, and the method loops back to 1501 to process the next received commanded movement of the camera instrument 211.

Figure 19:
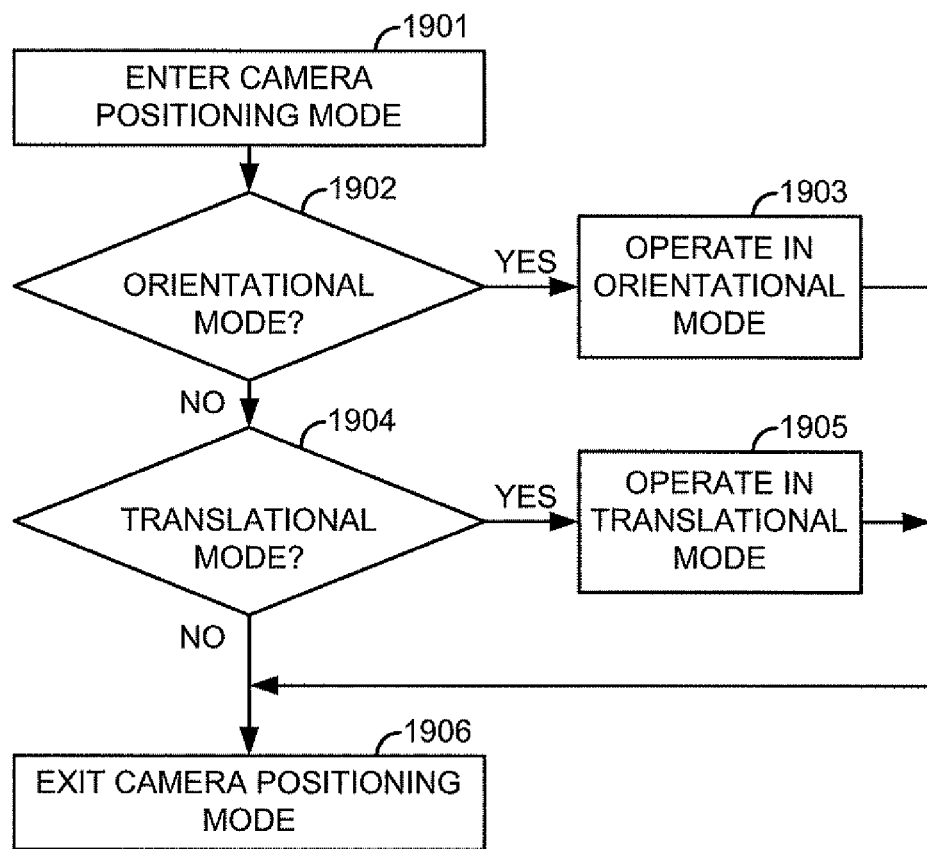
FIG. 19 illustrates a flow diagram of another alternative method for moving a camera in response to a movement of an input device of a medical robotic system, utilizing aspects of the present invention.

FIG. 19 illustrates, as an example, another method for moving the camera instrument 211 in response to the input device. In this method, in 1901, the operator may command the camera movement to enter the orientational mode by, for example, pushing the input devices 108, 109 towards each other, and command the camera movement to enter the translational mode by, for example, pulling the input devices 108, 109 away from each other. In particular, a haptic detent feature can be implemented on the virtual handle bar, so that the user has the perception of clicking a button along such bar in order to switch the camera control mode. In 1902, the method determines whether the operator has entered an orientational mode command. If the determination in 1902 is YES, then in 1903, the method moves the camera in response to translational movement of the input device in the orientational mode (as described in reference to 1503 of FIG. 15) and, upon completion, the algorithm jumps to 1906 to exit the camera positioning mode. If the determination in 1902 is NO, however, then in 1904, the method determines whether the operator has entered a translational mode command. If the determination in 1904 is YES, then in 1905, the method moves the camera in response to translational movement of the input device in the translational mode (as described in reference to 1504 of FIG. 15) and upon completion jumps to 1906 to exit the camera positioning mode. If the determination in 1904 is NO, however, then the camera positioning mode has apparently been entered in error and in 1906, the method exits the camera positioning mode.

Although the various aspects of the present invention have been described with respect to a preferred embodiment, it will be understood that the invention is entitled to full protection within the full scope of the appended claims.

What is claimed is:

1. A method comprising:
   receiving one or more operator inputs via one or more input devices;
   determining, by a controller based on one or more properties of the one or more operator inputs, if an orientational mode command or a translational mode command is entered;
   in response to determining that the orientational mode command is entered, constraining, by the controller, movement of an imaging device so that a focal point of the imaging device moves along a concave virtual surface in response to translational movement of the one or more input devices; and
   in response to determining that the translational mode command is entered, causing, by the controller, translational movement of the imaging device in a three-dimensional space in response to the translational movement of the one or more input devices.

2. The method of claim 1, wherein determining if the orientational mode command or the translational mode command is entered comprises using a dynamic filter.

3. The method of claim 1, further comprising: maintaining, by the controller, orientational alignment between the one or more input devices and one or more respective instruments while responding to the translational movement of the one or more input devices.

4. The method of claim 1, wherein determining if the orientational mode command or the translational mode command is entered comprises:
   determining that the orientational mode command is entered in response to detecting that a first input device of the one or more input devices and a second input device of the one or more input devices are being moved toward each other; or
   determining that the translational mode command is entered in response to detecting that the first input device and the second input device are being moved away from each other.

5. The method of claim 1, wherein determining if the orientational mode command or the translational mode command is entered comprises:
   determining that the orientational mode command is entered in response to detecting that a magnitude of commanded movement of the imaging device is below a first threshold; or
   determining that the translational mode command is entered in response to detecting that the magnitude of commanded movement of the imaging device is above a second threshold, the second threshold being equal to or higher than the first threshold.

6. The method of claim 1, wherein determining if the orientational mode command or the translational mode command is entered comprises:
   determining that the orientational mode command is entered in response to detecting that a magnitude of commanded movement of the imaging device is below a first threshold; and
   determining that the translational mode command is entered in response to detecting that the magnitude is above a second threshold, the second threshold being equal to or higher than the first threshold.

7. The method of claim 1, further comprising:
   in response to determining that a transitional mode command is entered:
      decomposing, by the controller, the translational movement of the one or more input devices into a rotational motion command for the imaging device and a translational motion command for the imaging device; and
      causing, by the controller, the imaging device to move according to the rotational motion command and the translational motion command.

8. The method of claim 7, wherein decomposing the translational movement comprises: applying a dynamic filter.

9. The method of claim 7, wherein determining that the transitional mode command is entered comprises: determining that a magnitude of commanded movement of the imaging device is above a first threshold and below a second threshold.

10. The method of claim 9, wherein determining if the orientational mode command or the translational mode command is entered comprises:
    determining that the orientational mode command is entered in response to detecting that the magnitude is below the first threshold; and
    determining that the translational mode command is entered in response to detecting that the magnitude is above the second threshold.

11. A system comprising:
    a manipulator configured to support an imaging device; and
    a controller coupled to the manipulator and configured to:
       receive one or more operator inputs via one or more input devices;
       determine, based on one or more properties of the one or more operator inputs, if an orientational mode command or a translational mode command is entered;
       in response to determining that the orientational mode command is entered, constrain movement of the imaging device using the manipulator so that a focal point of the imaging device moves along a concave virtual surface in response to translational movement of the one or more input devices; and
       in response to determining that the translational mode command is entered, cause, using the manipulator, translational movement of the imaging device in a three-dimensional space in response to the translational movement of the one or more input devices.

12. The system of claim 11, wherein to determine if the orientational mode command or the translational mode command is entered, the controller is configured to: use a dynamic filter.

13. The system of claim 11, wherein the controller is further configured to:
    maintain orientational alignment between the one or more input devices and one or more respective instruments supported by the system while responding to the translational movement of the one or more input devices.

14. The system of claim 11, wherein to determine if the orientational mode command or the translational mode command is entered, the controller is configured to:
    determine that the orientational mode command is entered in response to detecting that a first input device of the one or more input devices and a second input device of the one or more input devices are being moved toward each other; or
    determine that the translational mode command is entered in response to detecting that the first input device and the second input device are being moved away from each other.

15. The system of claim 11, wherein to determine if the orientational mode command or the translational mode command is entered, the controller is configured to:
  determine that the orientational mode command is entered in response to detecting that a magnitude of commanded movement of the imaging device is below a first threshold; or
  determine that the translational mode command is entered in response to detecting that the magnitude is above a second threshold, the second threshold being equal to or higher than the first threshold.

16. The system of claim 11, wherein the controller is further configured to:
  in response to determining that a transitional mode command is entered:
    decompose the translational movement of the one or more input devices into a rotational motion command for the imaging device and a translational motion command for the imaging device; and
    cause, using the manipulator, the imaging device to move according to the rotational motion command and the translational motion command.

17. A controller comprising hardware and software implemented components, the hardware and software implemented components comprising:
  a receiving component configured to receive one or more operator inputs via one or more input devices;
  a determining component configured to determine, based on one or more properties of the one or more operator inputs, if an orientational mode command or a translational mode command is entered;
  a movement component configured to:
    in response to determining that the orientational mode command is entered, constrain movement of an imaging device so that a focal point of the imaging device moves along a concave virtual surface in response to translational movement of the one or more input devices, and
    in response to determining that the translational mode command is entered, cause translational movement of the imaging device in a three-dimensional space in response to the translational movement of the one or more input devices.

18. The controller of claim 17, wherein to determine if the orientational mode command or the translational mode command is entered, the determining component is configured to:
  determine that the orientation mode command is entered in response to detecting that a first input device and a second input device are being moved toward each other; or
  determine that the translational mode command is entered in response to detecting that the first input device and the second input device are being moved away from each other.

19. The controller of claim 17, wherein to determine if the orientational mode command or the translational mode command is entered, the determining component is configured to:
  determine that the orientational mode command is entered in response to detecting that a magnitude of commanded movement of the imaging device is below a first threshold; or
  determine that the translational mode command is entered in response to detecting that the magnitude of commanded movement of the imaging device is above a second threshold, the second threshold being equal to or higher than the first threshold.

20. The controller of claim 17, wherein the determining component is further configured to, in response to determining that a transitional mode command is entered:
  decompose the translational movement of the one or more input devices into a rotational motion command for the imaging device and a translational motion command for the imaging device; and
  cause the imaging device to move according to the rotational motion command and the translational motion command.

* * * * *